Figure 1:
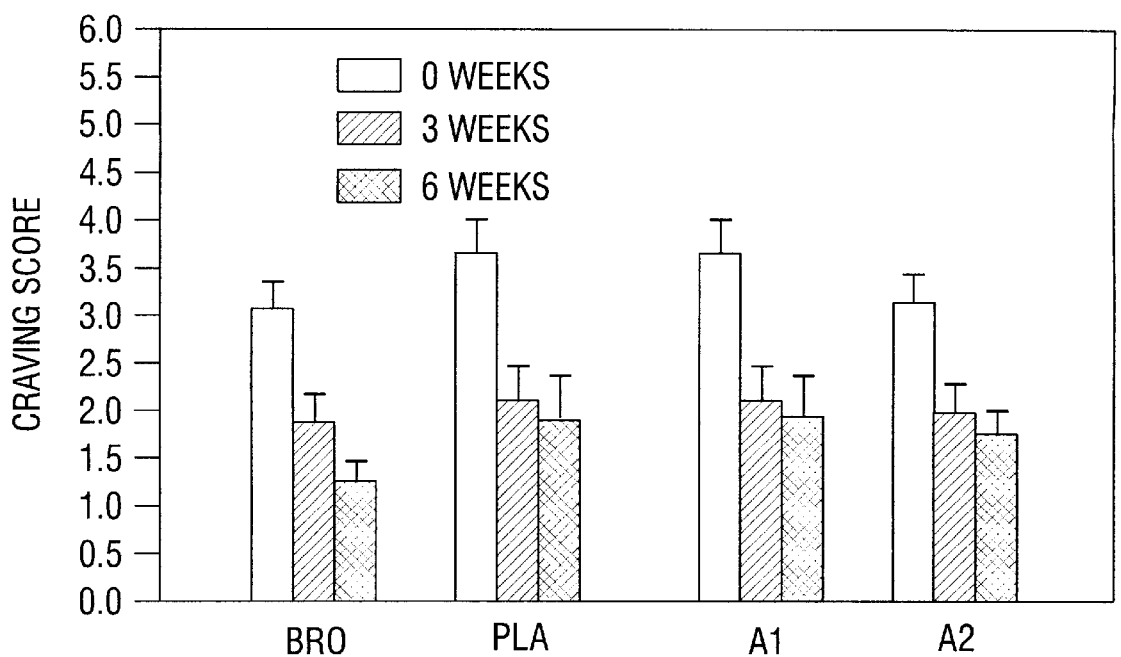

United States Patent [19]

Noble

[11] Patent Number: 6,001,848
[45] Date of Patent: Dec. 14, 1999

[54] BROMOCRIPTINE FOR THE TREATMENT OF ALCOHOLICS DIAGNOSED WITH THE $D_2$ DOPAMINE RECEPTOR DRD2 A1 ALLELE

[75] Inventor: Ernest P. Noble, South Laguna, Calif.

[73] Assignee: The Regents of the University of California, Los Angeles, Calif.

[21] Appl. No.: 08/822,659

[22] Filed: Mar. 24, 1997

Related U.S. Application Data

[60] Provisional application No. 60/014,136, Mar. 25, 1996.

[51] Int. Cl.⁶ .................................................. A61K 31/44
[52] U.S. Cl. ........................ 514/288; 514/282; 514/284; 514/651; 514/811
[58] Field of Search .................................. 514/282, 284, 514/288, 651, 811

[56] References Cited

U.S. PATENT DOCUMENTS

| | | | |
|---|---|---|---|
| 4,882,335 | 11/1989 | Sinclair | 514/282 |
| 5,210,016 | 5/1993 | Blum et al. | 435/6 |
| 5,298,622 | 3/1994 | Portoghese et al. | 546/15 |
| 5,500,343 | 3/1996 | Blum et al. | 435/6 |
| 5,550,021 | 8/1996 | Blum et al. | 435/6 |

FOREIGN PATENT DOCUMENTS

| | | |
|---|---|---|
| 2037353 | 6/1992 | Canada . |
| 0 346 830 | 5/1995 | European Pat. Off. . |
| 9609047 | 3/1996 | WIPO . |

OTHER PUBLICATIONS

O'Malley et al., "Naltrexone and Coping Skills Therapy for Alcohol Dependence," *Arch. Gen. Psychiatry*, 49:881–887, Nov. 1992.

McBride et al., "Serotonin, Dopamine and GABA Involvement in Alcohol Drinking of Selectively Bred Rats," *Alcohol*, 7:199–205, 1990.

Dyr et al., "Effects of $D_1$ and $D_2$ Dopamine Receptor Agents on Ethanol Consumption in the High–Alcohol–Drinking (HAD) Lines of Rats," *Alcohol*, 10:207–212, 1993.

Rassnick et al., "SDZ–205, 152, a Novel Dopamine Receptor Agonist, Reduces Oral Ethanol Self–Administration in Rats," *Alcohol*, 10:127–132, 1993.

Uhl et al., "Substance Abuse Vulnerability and $D_2$ Receptor Gene," *Trends Neurosci.*, 16:83–88, 1993.

Weiss et al., "Free–Choice Responding for Ethanol Versus Water in Alcohol Preferring (P) and Unselected Wistar Rats is Differentially Modified by Naloxone, Bromocriptine and Methysergide," *Psychopharmacology*, 101:178–186, 1990.

Noble, "The $D_2$ Dopamine Receptor Gene: A Review of Association Studies in Alcoholism," *Behav. Genet.*, 23:119–129, 1993.

Noble and Blum, "Alcoholism and the $D_2$ Receptor Gene (Letter)," *J. Am. Med. Assoc.*, 270;1547, Oct. 1993.

Noble et al., "Allelic Association of the $D_2$ Dopamine Receptor Gene with Receptor–Binding Characteristics in Alcoholism," *Arch. Gen. Psychiatr.*, 48:648–654, Jul. 1991.

Noble et al., "Allelic Association of the $D_2$ Dopamine Receptor Gene with cocaine Dependence," *Drug. Alc. Depend.*, 33:271–285, 1993.

Noble et al. "Prolonged P300 latency in children with the $D_2$ dopamine receptor A1 allele," *Am. J. Hum. Genet.*, 54:658–668, 1994.

Noble et al., "$D_2$ dopamine receptor gene and obesity," *Int. Eating Disord.*, 15:205–217, 1994.

Noble et al., "$D_2$ Dopamine Receptor Gene and Cigarette Smoking: A Reward Gene?" *Med. Hypotheses*, 42:257–260, 1994.

Berman and Noble, "Reduced Visuospatial Performance in Children with the $D_2$ Dopamine Receptor A1 Allele," *Behav. Genet.*, 25:45–48, 1995.

Benjamin et al., "Naltrexone Reverses Ethanol–Induced Dopamine Release in the Nucleus Accumbens in Awake, Freely Moving Rats," *Brain Res.*, 621:137–140, 1993.

Bohn et al., "Naltrexone and Brief Counseling to Reduce Heavy Drinking," *Am. J. Addictions*, 3:91–99, 1994.

Borg, "Bromocriptine in the prevention of alcohol abuse," *Acta Psychiat. Scand.*, 68:100–111, 1983.

Borg and Weinholdt, "A Preliminary Study of Two Dopaminergic Drugs, Apomorphine and Bromocriptine (Parlodel), in the Treatment of the Alcohol–Withdrawal Syndrome," *Curr. Ther. Res.*, 27:170–177, Feb. 1980.

Borg and Weinholdt, "Bromocriptine in the Treatment of the Alcohol–Withdrawal Syndrome," *Acta Psychiat. Scand.*, 65:101–111, 1982.

Dongier et al., "Bromocriptine in the Treatment of Alcohol Dependence," *Alcoholism*, 15:970–977, Nov./Dec. 1991.

Powell et al., "A Double–Blind, Placebo–Controlled Study of Nortriptyline and Bromocriptine in Male Alcoholic Subtyped by Comorbid Psychiatric Disorders," *Alcoholism*, 19:463–468, Apr. 1995.

Liskow and Goodwin, "Pharmacological Treatment of Alcohol Intoxication, Withdrawal and Dependence: A Critical Review," *J. Stud. Alcohol*, 48:356–370, 1987.

Litten and Allen, "Pharmacotherapies for Alcoholism: Promising Agents and Clinical Issues," *Alcoholism*, 15:620–633, Jul./Aug. 1991.

Gorelick, "Medications for the Treatment of Substance Abuse," *Curr. Opin. Psychiatr.*, 5:430–435, 1992.

Lawford et al., "Bromocriptine in the treatment of alcoholics with the $D_2$ dopamine receptor A1 allele," *Nature Med.*, 1:337–341, Apr. 1995.

(List continued on next page.)

*Primary Examiner*—M. Moezie
*Attorney, Agent, or Firm*—Arnold, White & Durkee

[57] ABSTRACT

Disclosed are dopamine agonist and opioidergic compositions and methods for their use in the treatment of alcoholism. The invention discloses compounds and therapeutic kits useful in the treatment of alcoholics having the A1 allele of the dopamine receptor D2 gene. Also disclosed are methods of treating alcoholics having the A1/A1 or A1/A2 DRD2 genotype comprising administration of dopamine agonists such as aporphines, ergolines, related compounds, and their analogs, in combination with opioidergic compounds such as naloxone.

4 Claims, 4 Drawing Sheets

OTHER PUBLICATIONS

O'Brien, "Rat study sheds light on cocaine craving", *Science,* 271:1499, Mar. 1996.

Parkes, "Medical intelligence: drug therapy: bromocriptine", *New Engl. J. Med.,* 301:873–878, 1979.

Muller and Cramon, "Dopaminergic stimulation of brain damaged patients with bromocriptine and pergolide: a pharmacological approach to treat attentional deficits and apathy?" *Neuropschychopharmacology,* 10:3S:175S, May, 1994, (P–117–88).

Dackis et al., "Single–dose bromocriptine reverses cocaine craving", *Psych. Res.,* 20:261–264, 1987.

Tennant and Sagherian, "Double–blind comparison of amantadine and bromocriptine for ambulatory withdrawal from cocaine dependence", *Arch. Intern. Med.,* 147:109–112, Jan. 1987.

Anton, "New directions in the pharmacotherapy of alcoholism", *Psychiatric Annals,* 25:6:353–362, Jun. 1995.

Giannini et al., "Bromocriptine and amantadine in cocaine detoxification", *Psychiatry Res.,* 29:11–16, 1989.

Dackis et al., "Bromocriptine treatment for cocaine abuse: the dopamine hypothesis", *Intl. J. Psychiatr. Med.,* 15(2):125–135, 185–86.

Hitzig, "Combined dopamine and serotonin agonists: A synergistic approach to alcoholism and other addictive behaviors", *Maryland Medical Journal,* 42:153–157, Feb. 1993.

Hubner and Koob, "Bromocriptine produces decreases in cocaine self–administration in the rat", *Neuropsychopharmacology,* 3:101–108, 1990.

Naeger and Martinez, "The effect of tetrahydropapaveroline, bromocriptine, haloperidol, and lithium on voluntary ethanol ingestion", *Proc. West. Pharmacol. Soc.,* 33:205–208, 1990.

Goldman, "Bromocriptine in the treatment of alcoholics", (letter to editor) *Nature Medicine,* 1:720, Aug. 1995.

Noble et al., "Bromocriptine in the treatment of alcoholics", (reply to Golman letter) *Nature Medicine,* 1:720–1, Aug. 1995.

Ng and George, "Dopamine receptor agonist reduces ethanol self–administration in the ethanol–preferring C57BL/6J inbred mouse", *European Journal of Pharmacology,* 269:365–374, 1994.

Uzbay et al., "Effects of bromocriptine and haloperidol on ethanol withdrawal syndrome in rats", *Pharmacology Biochemistry and behavior,* 49:969–974, 1994.

Manopulo et al., "Management of alcohol withdrwal syndrome experience with bromocriptine", *Clinica Terapeutica,* 116:297–302, 1986.

Burroughs et al., "Double–blind controlled trial of bromocriptine, chlordiazepoxide and chlormethiazole for alcohol withdrawal symptoms", *Alcohol & Alcoholism,* 20:263–271, 1985.

Nuotto and Mattila, "Failure of amantadine and bromocriptine to counteract alcoholic inebriation in man", *Acta pharmacol. et toxicol.,* 55:168–173, 1984.

Neiswanger et al., "What can the DRD2/alcoholism story teach us about association studies in psychiatric genetics?", *American Journal of Medical Genetics (Neuropsychiatric Genetics),* 60:272–275, 1995.

Neiswanger et al., "Association and linkage studies of the TAQI A1 allele at the dopamine $D_2$ receptor gene in samples of female and male alcoholics", *American Journal of Medical Genetics (Neuropsychiatric Genetics),* 60:267–271, 1995.

DOPAMINE

GROUP 1

APOMORPHINE

GROUP 2

PERGOLIDE

GROUP 3

BROMOCRIPTINE

GROUP 4

LISURIDE

BROMOCRIPTINE FOR THE TREATMENT OF ALCOHOLICS DIAGNOSED WITH THE D₂ DOPAMINE RECEPTOR DRD2 A1 ALLELE

The present application is a continuing application based on U.S. Provisional Patent Ser. No. 60/014,136, filed Mar. 25, 1996, the entire content of which is incorporated herein by reference.

BACKGROUND OF THE INVENTION

1.1 FIELD OF THE INVENTION

The present invention relates generally to the field of molecular biology. More particularly, certain embodiments comprise dopamine agonist compositions and methods for their use in the treatment of alcoholism and related compulsive disorders. In preferred embodiments methods and compositions are disclosed for the treatment of patients having the A1 allele of the $D_2$ dopamine receptor (DRD2) gene.

1.2 DESCRIPTION OF THE RELATED ART

1.2.1 TREATMENT OF ALCOHOLISM

A variety of effective drugs are now available in the treatment of many mental afflictions including schizophrenia, anxiety reactions and affective disorders. In contrast, with the recent exception of naltrexone, vide infra, no current accepted pharmacotherapy exists for decreasing alcohol consumption and relapse in alcoholics (for reviews see Noble, 1984; Liskow and Goodwin, 1987; Litten and Allen, 1991; Gorelick, 1992).

A variety of methods have been described in the literature in recent years relating to treatment of chronic alcoholism. Such methods have included stimulating electroacupuncture of zones in the ears (Soviet Pat. No. SU 1,757,671, 1992); intramuscular injection of meksidol (Soviet Pat. No. SU 1,777,878, 1992); oral compositions which contain vitamin, protein, fat and carbohydrate compounds (Soviet Pat. No. SU 1,717,069, 1992); visual stimulation using pulsed red light (Soviet Pat. No. SU 1,699,467, 1991); peroral administration of vitamin complexes and honey (Soviet Pat. No. SU 1,697,802, 1991); intravenous injection of cholecystokinin (Soviet Pat. No. SU 1,463,302, 1989); administration of phenylalkanoyl amines (European Pat. No. EP 424,528, 1992); administration of opiod antagonists (Intl. Pat. Appl. Publ. No. WO 960947, 1996); administration of spiroindane derivatives (U.S. Pat. No. 5,298,622, 1994); application of low frequency alternating currents to reflect reflexogenic zones (Russian Pat. No. RU 2,056,110, 1996); a variety of homeopathic compositions including sulfur and rattlesnake venom (Russian Pat. No. RU 2,039,561, 1995); -apomorphine-teturam administration (Soviet Pat. No. SU 1,806,743, 1993); and a variety of treatment methods involving acute negative reaction and somatic disturbance (Soviet Pat. No. SU 170,148; 1968). Each of the aforementioned patents is specifically incorporated herein by reference in its entirety.

Although significant literature exists on the use of various compounds for the treatment of alcoholics, results to date have been sporadic, unpredictable, and a majority of the tests have been limited to theoretical considerations.

European Patent EP 0346830 and corresponding U.S. Pat. No. 4,882,335 (each specifically incorporated herein by reference) report the possible use of naltrexone and naloxone for the treatment of alcoholism in humans, although the data presented was limited to decreased drinking of alcohol by rats following administration of naloxone or naltrexone.

Intl. Pat. Appl. Publ. No. WO 9609047A1 (specifically incorporated herein by reference) discloses a method for treating alcoholism in a mammal using a combination of opioid antagonists and serotonin reuptake inhibitors.

However, with the burgeoning advances in the neurosciences and molecular genetics, the time is propitious to apply this cumulative knowledge to the effective treatment of alcoholism.

1.2.2 ALCOHOL AND THE DOPAMINERGIC SYSTEM

Alcohol, like other substances of abuse, induces euphoria and pleasurable feelings in users. It has been hypothesized that these positive reinforcement effects are manifested through activation of the mesolimbic dopaniinergic reward pathways of the brain (for reviews see Wise and Rompre, 1989; Koob, 1992). In support of this hypothesis is a substantial body of physiological, neurochemical, pharmacological and behavioral evidence. Thus, alcohol, administered both in vivo and in vitro, dose-dependently increases the firing rate of dopaminergic neurons in the ventral tegmental area (VTA) of the brain, indicating that the drug activates the mesoaccumbens dopaminergic system (Gessa et al., 1985; Brodie et al., 1990). These observations are consistent with several studies showing that low doses of systematically and locally administered ethanol increases dopamine (DA) release in a calcium-dependent manner from the nucleus accumbens (NAC) in awake rats (Imperato and Di Chiara, 1986; Wozniak et al., 1991; Yoshimoto et al., 1991; Weiss et al., 1993). That the dopaminergic system is implicated in alcohol-related behaviors also comes from brain lesion studies. Following circumscribed ablation of dopaminergic neurons within either the NAC or tuberculum olfactorium (TO), preference for ethanol significantly increased in rats (Quarfordt et al., 1991). The authors of this report (Quarfordt et al., 1991) suggest that one of the functional roles for the dopaminergic neurons of the NAC and TO is to regulate the craving for a drug with addictive liability such as ethanol.

A role for the dopaminergic system in ethanol preference is also suggested by data from animal genetic models of alcoholism. DA concentrations in the NAC of alcohol preferring (P) rats were found to be significantly lower when compared to alcohol non-preferring (NP) rats (Murphy et al., 1987; Gongwer et al., 1989). More recently, two independent studies of alcohol-naive P and NP rats have shown that the maximum number of binding sites ($B_{MAX}$) of the $D_2$ dopamine receptor to be significantly reduced in the NAC and caudate nucleus of P compared to NP rats (Stefanini et al., 1992; McBride et al, 1993). It is suggested (Stefanini et al., 1992) that one possible interpretation of the reduced $D_2$ numbers in the P rats is that it may reflect a parallel reduction in dopaminergic neurotransmission in limbic areas of the brain. To compensate for this deficit, the P rats consume more alcohol in order to release enough DA to produce an adequate level of reward.

Whereas ethanol consumption involves several brain neurotransmitters including norepinephrine (Ahlenius et al., 1973; Amit and Brown, 1982; Brown and Amit, 1977; Corcoran et al., 1983; Davis et al., 1979; Murphy et al., 1985), serotonin (McBride et al., 1988; Murphy et al., 1988) and GABA (Hwang et al., 1990; McBride et al., 1990), growing evidence, derived from the administration of neurotransmitter receptor agonists and antagonists, further supports an important role for the dopaminergic system in mediating the stimulating reinforcing effects of ethanol.

1.2.3 DOPAMINE AGONISTS AND DECREASED ALCOHOL INTAKE IN RATS

Decreases in alcohol intake of P and High-Alcohol-Dinking (HAD) rats were found after the administration of the $D_2$ agonists bromocriptine (McBride et al., 1990) and quinpirole (Dyr et al., 1993). In another study (Weiss et al., 1990), the differential effects of naloxone (an opiate antagonist), bromocriptine and methysergide (a 5-HT antagonist) on ethanol consumption was compared in P and unselected Wistar rats. In P rats, naloxone treatment resulted in a dose-dependent suppression in responding for both ethanol and water, but did not alter ethanol preference. This suggests that the response decrements observed with naloxone was reflective of a more general depression in consummatory behavior. In contrast, bromocriptine produced a significant, dose-dependent shift in preference from ethanol toward water by inhibiting responding for ethanol while enhancing water consumption. In the Wistar rats, naloxone and bromocriptine treatments produced changes in ethanol preference patterns similar to but less than those observed with methysergide. Furthermore, a recent study (Rassnick et al., 1993) has determined the effects of a novel dopamine receptor agonist (SDZ-205, 152) in rats trained to orally self-administer ethanol. The results of this study showed that administration of this dopamine agonist selectively reduced ethanol-reinforced responding without affecting responses for water.

1.2.4 APOMORPRINE AND ALCOHOL DEPENDENCE IN HUMANS

Studies of humans provide additional support to connections between alcohol dependence and CNS dopaminergic function. Neuroendocrine evidence for reduced dopamine receptor sensitivity in alcoholics has been found. Using apomorphine (APO), a $D_2$ agonist, the maximal growth hormone (GH) response was found to be significantly reduced in alcoholics who were 2 months (Balldin et al., 1992) and more than 6 years (Balldin et al., 1993) abstinent compared to controls. It was suggested that the reduced $D_2$ receptor function in alcoholics was a trait marker for this disorder, although the possibility that this reduction is acquired after earlier periods of heavy alcohol consumption cannot be ruled out. Heinz et al., (1995) compared GH response to APO in relapsed (active) and in abstinent (recovering) alcoholics. Despite the fact that both groups had similar prior alcohol consumption history and no other clinical data differentiated these groups, the relapsed alcoholics had a more blunted GH response compared to abstinent alcoholics. Additionally, Weisbeck et al. (1995) determined GH response to APO in controls and in alcoholics who were either family history positive or negative for alcoholism. The blunted response in the positive but not the negative group was significantly different when compared to controls. These authors suggest that the reduced $D_2$ receptor function in family history positive alcoholics may be a genetically influenced trait marker. Finally, very recent imaging studies including PET (Hietela et al., 1994) and SPECT (Tiihonen et al., 1995) analyses have shown a reduced central dopaminergic function in chronic non-violent alcoholics compared to controls.

1.2.5 EARLY STUDIES USING BROMOCRIPTINE

At least three early studies (Morgan et al., 1980; Morgan, 1981; Anokhina, 1984) have investigated the use of bromocriptine for the treatment of alcoholism in humans, but the data were not controlled. In another study of 60 alcoholics, randomly assigned to bromocriptine (2.5 mg tid) or placebo, the bromocriptine group compared to the placebo group showed a greater amelioration of withdrawal symptoms over the 10-day trial (Borg and Weinholdt, 1982). In the first double-blind bromocriptine/placebo study, 50 alcoholics, randomly assigned to bromocriptine (2.5 mg tid, months 1–3; 5 mg tid, months 4–6) or placebo were evaluated for 6 months (Borg, 1983). The overall effects on the number and duration of drinking episodes, psychological status and social functioning were significantly improved in the bromocriptine compared to the placebo group. Rater global evaluation of medication effect was assessed as moderate to very beneficial in 16 of 19 bromocriptine administered patients and in one of 23 placebo administered patients. The incidence of adverse reactions was low in both groups, and the higher dose of bromocriptine (15 mg/day) was no better than the lower dose (7.5 mg/day) in treatment outcome. In a second double-blind controlled study (Dongier et al., 1991), 84 alcoholics received either bromocriptine (2.5 mg tid) or placebo and were followed for two months. Drinking behavior showed a marked improvement in both the bromocriptine and placebo treated groups. Moreover, significant differences in favor of the medication were observed in psychopathological measures, and trends in the same direction in most of the other iffcacy measures.

In a third double-blind trial, alcoholics were given either bromocriptine (2.5 mg) tid, months 1–3; 5 mg tid, months 4–6) or placebo for six months (Powell et al., 1995). Alcoholics were divided, according to the authors, into three "not pure" subtypes: 1) "pure alcoholics," 2) alcoholics who had comorbid affective or anxiety disorders but not antisocial personality disorders (APD) and 3) alcoholics who had comorbid APD but were with or without Axis I disorders. Thirty-four alcoholics on bromocriptine and 31 alcoholics on placebo completed the trial. Analysis of data showed a significant decrease in anxiety (Beck Anxiety Inventory) and a trend in reduced craving and drinking days only in APD alcoholics receiving bromocriptine compared to APD alcoholics receiving placebo.

Thus while the early studies support a role for the use of bromocriptine in the treatment of certain aspects of alcoholism, relatively few patients were studied or remained in the trial, the reliability and validity of most of the measures used to assess outcome were not reported, and patient compliance to the bromocriptine schedule was not done.

1.2.6 OPIOIDERGIC AND DOPAMINERGIC SYSTEMS

There is growing evidence that the opioidergic and dopaminergic systems are anatomically and functionally interconnected. Nigrostriatal dopaminergic afferents have direct input into the opioidergic (enkephalinergic) neurons of the striatum (Kubota et al., 1986), and all detectable enkephalin neurons in the striatum contain the $D_2$ dopamine receptor mRNA (Le Moine et a., 1990). Moreover, dopamine antagonists and lesions of the dopaminergic pathways in the brain affect preproenkephalin A activity (Morris et al., 1988; Normand et al., 1988).

Behavioral, pharmacological and neurochemical studies implicate the opioidergic and dopaminergic systems in the reinforcing effects of ethanol and other drugs of abuse (Koob and Bloom, 1988). Animal studies show that opiate receptor agonists increase preference for ethanol (Volpicelli et al., 1992; Wild and Reid, 1990), whereas antagonists of these receptors reduce ethanol consumption (Le et al., 1993; Myers et al., 1986). Further, studies on human alcoholics suggest the effectiveness of the opiate receptor antagonist naltrexone in reducing the positive reinforcing effects of alcohol consumption (O'Malley et al., 1992; Swift et al., 1985; Volpicelli et al., 1992). Moreover, ethanol-induced increase of brain dopamine levels in animals is blocked by both opiate receptor antagonists naloxone (Widdowson and Holman, 1992) and naltrexone (Benjamin et al., 1993). The gathering evidence suggests an essential role for the endogenous opioidergic system in mediating the effects of ethanol on brain dopamine pathways associated with reward.

1.2.7 NALTREXONE IN THE TREATMENT OF ALCOHOLISM

Lopez-Ibor-Alino (1990), in an uncontrolled naltrexone trial in an opiate treatment program, found that patients on regimens of naltrexone increased their alcohol use. In sharp contrast, however, other studies have shown the opposite effect. Volpicelli et al., (1992), in a double-blind, placebo-controlled trial, studied the effect of naltrexone in 70 male outpatient alcoholics. During the 12-week study, only 23% of naltrexone-treated subjects met the criteria of relapse, whereas 54.3% of the placebo-treated subjects relapsed. Moreover, subjects taking naltrexone reported significantly less alcohol craving and days in which any alcohol was consumed. In an accompanying article, O'Malley et al. (1992), also in a double-blind, placebo-controlled trial, studied 97 alcoholics receiving supportive therapy or coping skills therapy over a 12-week period. They found that naltrexone proved superior to placebo in measures of drinking and alcohol-related problems, including abstention rates, number of drinking days, relapse and severity of alcohol-related problems. Moreover, those patients who initiated drinking and who had received naltrexone and coping skills therapy were the least likely to relapse. Bohn et al. (1994) conducted a single-blind study with two doses of naltrexone and found reduced drinking by alcoholics.

Mason et al. (1994), in a double-blind, placebo-controlled pilot trial, studied the effects of nalmefene (a new opiate antagonist and structurally similar to naltrexone) in 21 alcoholics. Nalmefene lowered the rate of relapse and decreased the number of drinks/drinking days when compared to the placebo group. A very recent study by Volpicelli et al. (1995) presented data on their previously studied alcoholics (Volpicelli et al, 1992) who deviated from abstinence. Of the 36 subjects who reported a slip from abstinence, 12 naltrexone- and 17 placebo-treated alcoholics were available for assessment. The week of their first reported slip averaged around week 3 for both groups with no significant difference between the two groups. However, the placebo subjects drank more alcohol during the first lapse than did the naltrexone-treated subjects (P<0.05). Moreover, retrospective self-reports showed that a significantly larger proportion of naltrexone than placebo subjects experienced less high than usual after drinking alcohol (P=0.006). However, the reported levels of uncoordination, alcohol craving, memory disturbance and loss of temper did not differ between the naltrexone and placebo groups. Moreover, there were no significant correlations between these subjective variables and whether the subjects drank until they met relapse criterion.

How naltrexone exerts its effects in humans remains yet to be determined. In a recent study, Swift et al. (1994) quantified the effects of naltrexone on alcohol intoxication in nonalcoholic humans. They found less positive reinforcement and more intense sedative effects when the subjects received naltrexone and ethanol as compared to subjects who received placebo and ethanol. The combination of naltrexone and ethanol also induced nausea and vomiting in some of the subjects. These findings are consistent with the idea that naltrexone alters the subjective effects of ethanol. In particular, naltrexone reduces the positive reinforcing effects of ethanol intoxication and increases the negative reinforcing effects. Swift et al. (1994) suggest that these changes may underlie the observed decrease in ethanol drinking reported in the above clinical trials.

The neurochemical mechanisms through which naltrexone exerts its effects in humans remain unclear. Whereas the above cited clinical studies suggest the involvement of the opioidergic system, there is a substantial body of evidence from animal studies which indicates a connection between the opioidergic and dopaminergic system in the brain. For example, a recent report by Benjamin et al. (1993) shows that naltrexone and other opioid antagonists block the ethanol-induced release of dopamine in animals. If then, as cited earlier, the positive reinforcing effects of ethanol (and other substances of abuse) are manifested through activation of the mesolimbic dopaminergic pathways of the brain, then naltrexone, by blocking ethanol-induced release of dopamine, may diminish the reinforcing effects of alcohol.

In 1990, the present inventor and colleagues reported (Blum et al., 1990) a molecular genetic association with alcoholism. Specifically, the A1 (minor) allele of the $D_2$ dopamine receptor (DRD2) gene was found to be associated with severe alcoholics when compared to nonalcoholic controls. Subsequently, several studies, done in the U.S. and abroad, have further ascertained the role of this gene in alcoholism. Despite variations in the selection of subjects and other methodological issues, the combined evidence from these studies affirms the high prevalence of the A1 allele in alcoholics, especially when severe alcoholics are compared to nonalcoholic controls. Similarly, studies on cocaine addicts and polysubstance abusers have also found a high prevalence of the minor (A1 and B1) alleles of the DRD2 gene in these patients (Noble et al., 1993; Comings et al., 1991; Smith et al., 1992). Binding studies on the brains of deceased subjects showed that those carrying the A1 (minor) allele had reduced number of $D_2$ receptors than those carrying the A2 (major) allele (Noble et al., 1991). Moreover, in recent neurophysiological Noble et al., 1994c) and neuropsychological (Berman and Noble, 1995) studies of alcohol- and other drug-naive children, evidence also suggests a reduced dopaminergic function in subjects carrying the A1 allele compared to those having only the A2 allele. Put together, the emerging data suggest that subjects who inherit the A1 allele have an inherent deficit of their brain dopaminergic system.

1.3 DEFICIENCIES IN THE PRIOR ART

Alcoholism, a heterogeneous disorder with hereditary and environmental determinants, is a major health and social problem with a high recidivism rate. With the exception of the aversive agent disulfiram, no accepted pharmacotherapy now exits for the treatment of this disorder. The advent of molecular genetic techniques makes possible the identification of genetic types of alcoholics. Such identification renders feasible specific pharmacogenetic approaches to the treatment of hereditary forms of alcoholism.

A need to effectively treat alcoholics has long been recognized. To this end, several workers have treated this group of patients with various drugs; some that cause an aversion to alcohol (e.g., Anabuse®) while more recent treatments have investigated drugs that act as dopamine agonists. While some success has been reported in treating alcoholics with bromocryptine, the results did not indicate that such treatment was generally suitable for all alcohol addiction. Apparently there has not yet been an effort to first identify those subsets of patients appropriate for treatment with dopamine agonists, nor have any efforts been made to tailor drugs to interact specifically with receptor molecules in alcoholic patients identified with a genetic predisposition to alcohol abuse. Additionally, as with many drug regimens, there is not only a lack of specificity for universal treatment of alcoholics, there is also the problem of drug side effects. This is particularly so in the reported attempts to treat alcoholism where the limited success with certain dopamine agonists can be associated with inappropriate effects and/or interactions with other drugs.

2. SUMMARY OF THE INVENTION

The invention overcomes the limitations in the prior art by providing a method of identifying alcoholics which are suitable for treatment using dopaminergic or opioidergic compounds. The invention further provides for the design and selection of compounds i agonistic to a specific region of the dopamine receptor allele and particularly to those agonists that interact directly with the DRD2 allele. One class of compounds shown to be effective in this respect are dopamine agonists based on the bromocriptine structure. Other species generally include certain ergot derivatives and structural variations of nicotine and its analogs. The compounds are selected for their ability to bind to the DRD2 A1 allele, but not bind to DRD2 A2 allele receptors. In preferred embodiments methods and compositions for treating patients having the A1 allele of the DRD2 gene are disclosed.

In one important aspect, the invention provides a method of treating an alcoholic having the A1 allele of the DRD2 gene. The method generally comprises administering to the alcoholic a therapeutically-effective amount of a dopamine agonist or an opioidergic composition. Preferably, the A1 allele comprises either an A1/A1 or A1/A2 genotype. In preferred embodiments, the the dopamine agonist is an ergoline (such as bromocriptine, lisuride, or pergolide), or an aporphine, such as apomorphine or derivatives or salts thereof Preferred opioidergics include naloxone, naltrexone, cyclozzocine, diprenorphine, etazocine, levalorphan, metazocine, spiroindane, nalmefene, nalorphine, and salts, analogs, or derivatives thereof.

In a second embodiment, the treatment may further involve the administration of a serotonin reuptake inhibitor. Such an inhibitor may be fluoxetine, sertraline, paroxetine, fluvoxamine, venlafaxine, and nefazodone; or a salt or an analog or a derivative thereof.

A further aspect of the invention is a method of treating alcohol addiction. This method generally involves identifying an alcoholic subject having a DRD2 A1 allele; and administering to the subject an amount of a DRD2-specific dopamine agonist composition sufficient to alleviate said alcohol addiction. Preferably the A1 allele has an A1/A1 or A1/A2 genotype. Preferred dopamine agonists include ergolines or aporphines. Optionally, the method may further comprise the administration of a second agonist compound, or alternatively, the administration of one or more of the opioidergic compositions disclosed herein, either alone, or in combination with one or more of the serotonin reuptake inhibitors described herein. Preferably, the opioidergic compositions are naloxone, naltrexone, naloxone methoiodide, naloxonazine, naltrindole, naltrindole isothiocyanate, naltriben, norbinaltorphimine, funaltrexamine, cyprodime, cyclozzocine, diprenorphine, etazocine, levalorphan, metazocine, spiroindane, nalmefene, or nalorphine, or salts, analogs, or derivatives thereof. The serotoni reuptake inhibitors are preferably selected from the group consisting of fluoxetine, sertraline, paroxetine, fluvoxamine, venlafaxine, and nefazodone.

Another aspect of the invention, is a method of alleviating alcohol addiction in a human having a $D_2$ dopamine receptor A1 allele. This method generally involves obtaining nucleic acids from a blood sample of the subject; identifying in the nucleic acids a $D_2$ dopamine receptor A1 allele; and administering to the human an amount of a DRD2-specific dopamine agonist or opioidergic composition sufficient to alleviate the alcohol addiction. In preferred embodiments, the A1 allele genotype is either A1/A1 or A1/A2 genotype, and the preferred dopamine agonist is bromocriptine.

The method may further comprise administering to the human one or more opioidergic compositions either alone or in combination with one or more serotonin reuptake inhibitors.

2.1 IDENTICATION OF A1/A1 OR A1/A2 ALLELE ALCOHOLICS

Methods for the identification of $D_2$ dopamine receptor alleles in human subjects are well-known in the art, as evidenced by the teachings of U.S. Pat. Nos. 5,210,016; 5,500,343; and 5,550,021, each incorporated herein by reference in its entirety). The method generally involves obtaining sample nucleic acids from a patient, and identifing in the sample nucleic acids the DRD2 A1 allele. The genotype of such A1 allele patients may be either A1/A1, or A1/A2.

2.2 SELECTION OF DRD2 AGONISTS

One aspect of the invention concerns the identification of appropriate compounds for the development of treatment protocols for patients with alcohol dependence syndrome. Using genetic analysis techniques, alcohol dependent subjects may be selected for treatment with DRD2 agonists based on their allelic profile. Once the suitable profile is determined, such patients can be effectively treated for alcohol dependence by administration of selected DRD2 agonists. Preferably, the DRD2 allele is an A1 allele. The A1 allele may be of the A1/A1 or A1/A2 genotype. Dosages and methods of administration can be customized for the patient's age, sex and physical condition as well as compatibility with medications required for unrelated or ancillary medical conditions. It is anticipated that DRD2 receptors will be useful for tests to select new classes of agonists that may be structurally dissimilar to dopamine agonists but that nevertheless have the requisite binding or partial binding properties.

There are certain considerations that appear to be important in designing compositions which interact with the DRD2 receptor, and which particularly result in amelioration of alcoholic behavior in patients having the DRD2 A1 (or minor) allele. In addition to ergot-related structures such as the ergolines and their derivatives, aporphines and aporphine analogs are also expected to provide a suitable nucleus for modification. These compounds mimic dopamine to the extent of exhibiting ortho hydroxyl groups on an aromatic ring and it might be expected that bromo substituents will confer allelic specificity in a manner similar to that observed with bromocriptine. Other functional groups appear also to affect binding characteristics, particularly substituted ureas, secondary amides and thio ethers. In combination with rigid structures, these groups may be encouraged to bind with the DRD2 receptor. Rigid nuclei need not be aromatic; for example, bridged species such as adamantane or tricyclic compounds may provide any requisite rigidity.

2.3 SELECTION OF OPIOIDERGICS

The selection of opioidergics for use in the methods and compositions of the present invention are well-known to those of skill in the art. For example, the teachings of Intl. Pat Appl. Publ. No. WO 9609047A1, U.S. Pat. No. 5,298, 622, U.S. Pat. No. 4,882,235, each incorporated herein by reference in its entirety) provide one of skill in the art, having benefit of the present specification, to select opioidergic compounds which would be useful in the methods and compositions decribed herein. Preferred opioidergic compounds for use in the present invention include, but are not limited to, naloxone, naltrexone, naloxone methoiodide, naloxonazine, naltrindole, naltrindole isothiocyanate, naltriben, norbinaltorphirnine, funaltrexamine, cyprodime, cyclozzocine, diprenorphine, etazocine, levalorphan, metazocine, spiroindane, nalmefene, and nalorphine, spiroindane analogs (as exemplified in U.S. Pat. No. 5,298, 622, incorporated herein specifically by reference), or salts or analog thereof.

2.4 SELECTION OF SEROTONIN REUPTAKE INHIBTORS

The selection of serotonin reuptake inhibitors for use in the methods and compositions of the present invention are also well-known to those of skill in the art. For example, the teachings of Intl. Pat. Appl. Publ. No. WO 9609047A1, specifically incorporated herein by reference) provides one of skill in the art, having benefit of the present specification, to select serotonin reuptake inhibitory compounds which would be useful in the methods and compositions decribed herein. Preferred serotonin reuptake inhibitory compounds for use in the present invention include, but are not limited to, fluoxetine, sertraline, paroxetine, fluvoxamine, venlafaxine, and nefazodone, and salts or analogs thereof.

2.5 LIPOSOMES AND NANOCAPSULES

In certain aspects, administration of the compositions disclosed herein may be accomplished with pharmaceutical formulations of dopamine agonists in the form of liposomes or nanocapsules for either general administration or for specific targeting of areas of the brain containing DRD2 receptors. The formation and use of liposomes is generally known to those of skill in the art (see for example, Couvreur et al., 1977; 1988 which describes the use of liposomes and nanocapsules in the targeted antibiotic therapy of intracellular bacterial infections and diseases). Recently, liposomes were developed with improved serum stability and circulation half-times (Gabizon and Papahadjopoulos, 1988; Allen and Choun, 1987).

Liposomes have been used successfiully with a number of cell types that are normally resistant to transfection by other procedures including T cell suspensions, primary hepatocyte cultures and PC 12 cells (Muller et al., 1990). In addition, liposomes are free of the DNA length constraints that are typical of viral-based delivery systems. Liposomes have been used effectively to introduce genes, drugs (Heath and Martin, 1986; Heath et al., 1986; Balazsovits et al., 1989), radiotherapeutic agents (Pikul et al., 1987), enzymes (Imaizumi et al., 1990a; Imaizumi et al., 1990b), viruses (Faller and Baltimore, 1984), transcription factors and allosteric effectors (Nicolau and Gersonde, 1979) into a variety of cultured cell lines and animals. In addition, several successfuil clinical trails examining the effectiveness of liposome-mediated drug delivery have been completed (Lopez-Berestein et al., 1985a; 1985b; Coune, 1988; Sculier et al., 1988). Furthermore, several studies suggest that the use of liposomes is not associated with autoinmrune responses, toxicity or gonadal localization after systemic delivery (Mori and Fukatsu, 1992).

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 :m. Sonication of MLVs results in the formation of small unilamellar vesicles (SUVs) with diameters in the range of 200 to 500° C., containing an aqueous solution in the core.

Liposomes bear many resemblances to cellular membranes and are contemplated for use in connection with the present invention as carriers for the dopamine agonist compositions. They are widely suitable as both water- and lipid-soluble substances can be entrapped, i.e., in the aqueous spaces and within the bilayer itself, respectively. It is possible that the drug-bearing liposomes may even be employed for site-specific delivery of active agents by selectively modifying the liposomal formulation.

In addition to the teachings of Couvreur et al. (1977; 1988), the following information may be utilized in generating liposomal formulations. Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

In addition to temperature, exposure to proteins can alter the permeability of liposomes. Certain soluble proteins such as cytochrome c bind, deform and penetrate the bilayer, thereby causing changes in permeability. Cholesterol inhibits this penetration of proteins, apparently by packing the phospholipids more tightly. It is contemplated that the most useful liposome formations for antibiotic and inhibitor delivery will contain cholesterol.

The ability to trap solutes varies between different types of liposomes. For example, MLVs are moderately efficient at trapping solutes, but SUVs are extremely inefficient. SUVs offer the advantage of homogeneity and reproducibility in size distribution, however, and a compromise between size and trapping efficiency is offered by large unilameliar vesicles (LUVs). These are prepared by ether evaporation and are three to four times more efficient at solute entrapment than MLVs.

In addition to liposome characteristics, an important determinant in entrapping compounds is the physicochemical properties of the compound itself Polar compounds are trapped in the aqueous spaces and nonpolar compounds bind to the lipid bilayer of the vesicle. Polar compounds are released through permeation or when the bilayer is broken, but nonpolar compounds remain affiliated with the bilayer unless it is disrupted by temperature or exposure to lipoproteins. Both types show maximum efflux rates at the phase transition temperature.

Liposomes interact with cells via four different mechanisms: Endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. It often is difficult to determine which mechanism is operative and more than one may operate at the same time.

The fate and disposition of intravenously injected liposomes depend on their physical properties, such as size, fluidity and surface charge. They may persist in tissues for hours or days, depending on their composition, and half lives in the blood range from minutes to several hours. Larger liposomes, such as MLVs and LUVs, are taken up rapidly by phagocytic cells of the reticuloendothelial system, but physiology of the circulatory system restrains the exit of such large species at most sites. They can exit only in places where large openings or pores exist in the capillary endothelium, such as the sinusoids of the liver or spleen. Thus, these organs are the predominate site of uptake. On the other hand, SUVs show a broader tissue distribution but still are sequestered highly in the liver and spleen. In general, this in vivo behavior limits the potential targeting of liposomes to only those organs and tissues accessible to their large size. These include the blood, liver, spleen, bone marrow and lymphoid organs.

Targeting is generally not a limitation in terms of the present invention. However, should specific targeting be desired, methods are available for this to be accomplished. Antibodies may be used to bind to the liposome surface and to direct the antibody and its drug contents to specific antigenic receptors located on a particular cell-type surface. Carbohydrate determinants (glycoprotein or glycolipid cell-surface components that play a role in cell-cell recognition, interaction and adhesion) may also be used as recognition sites as they have potential in directing liposomes to particular cell types. Mostly, it is contemplated that intravenous injection of liposomal preparations would be used, but other routes of administration are also conceivable.

Alternatively, the invention provides for pharmaceutically-acceptable nanocapsule formulations of dopamine receptor agonists. Nanocapsules can generally entrap compounds in a stable and reproducible way (Henry-Michelland et al., 1987). To avoid side effects due to intracellular polymeric overloading, such ultrafine particles (sized around 0.1 :m) should be designed using polymers able to be degraded in vivo. Biodegradable polyalkyl-cyanoacrylate nanoparticles that meet these requirements are contemplated for use in the present invention, and such particles may be are easily made, as described (Couvreur et al., 1984; 1988).

2.6 DIAGNOSTIC/THERAPEUTIC KITS

In an important aspect, the invention provides a therapeutic kit comprising, in suitable container means, a therapeutically-effective amount of a DRD2-specific dopamine agonist, and a pharmaceutically acceptable excipient. Alternatively, the kit may farther provide one or more opioidergics and/or one or more serotonin reuptake inhibitors in a single or distinct container means. The compositions may be formulated such that they are suitable for oral or parenteral administration.

The diagnostic/therapeutic kits comprising the pharmaceutical compositions disclosed herein will generally contain, in suitable container means, a therapeutically-effective amount of a dopamine agonist in a pharmaceutically acceptable excipient. The kit may have a single container means that contains the dopamine agonist and a suitable excipient or it may have distinct container means for each compound.

The components of the kit may be provided as liquid solution(s), or as dried powder(s). When the components are provided in a liquid solution, the liquid solution is an aqueous solution, with a sterile aqueous solution being particularly preferred. When reagents or components are provided as a dry powder, the powder can be reconstituted by the addition of a suitable solvent. It is envisioned that the solvent may also be provided in another container means.

When the components of the kit are provided in one or more liquid solutions, the liquid solution is an aqueous solution, with a sterile aqueous solution being particularly preferred. The dopamine agonist(s) may also be formulated into a syringeable composition. In which case, the container means may itself be a syringe, or other such like apparatus, from which the formulation may be administered into the body, preferably by injection or even mixed with the other components of the kit prior to injection. The dopamine agonist to be administered may be a single agonist, or a composition comprising two or more agonists in a single or multiple dose for administration. Alternatively, one or more agonists may be administered consecutively or concurrently with other agents as deemed appropriate by the clinician. Dosage of each of the compositions will vary from subject to subject depending upon severity of conditions, size, body weight, etc. The calculation and adjustment of dosages of pharmaceutical compositions is well-known to those of skill in the art.

In an alternate embodiment, components of the kit may be provided as dried powder(s). When reagents or components are provided as a dry powder, the powder can be reconstituted by the addition of a suitable solvent. It is envisioned that the solvent may also be provided in another container means.

The container means will generally include at least one vial, test tube, flask, bottle, syringe or other container means, into which the dopamine agonist may be placed, preferably, suitably allocated. Where two or more agonists are provided, the kit will also generally contain a second vial or other container into which this additional agonists may be formulated. The kits may also comprise a second/third container means for containing a sterile, pharmaceutically acceptable buffer or other diluent.

The kits of the present invention will also typically include a means for containing the vials in close confinement for commercial sale, such as, e.g., injection or blow-molded plastic containers into which the desired vials are retained. Alternatively, the vials may be prepared in such a way as to permit direct introduction of the composition into an intravenous drug delivery system.

Irrespective of the number or type of containers, the kits of the invention may also comprise, or be packaged with, an instrument for assisting with the injection/administration or placement of the ultimate dopamine agonist composition within the body of an animal. Such an instrument may be a syringe, pipette, forceps, measured spoon, eye dropper or any such medically approved delivery vehicle.

Figure 4:
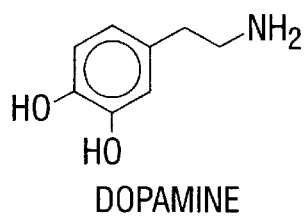
Figure 4:
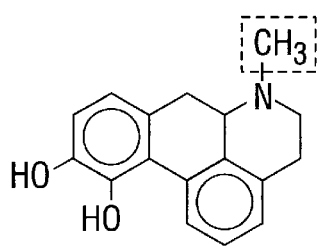
Figure 4:
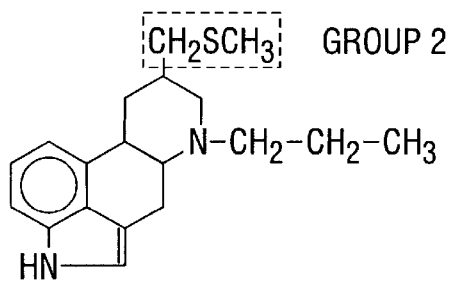
Figure 4:
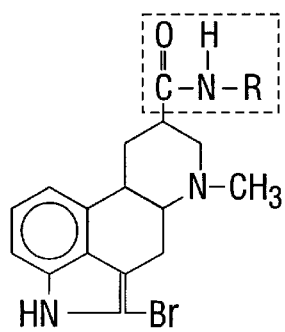
Figure 4:
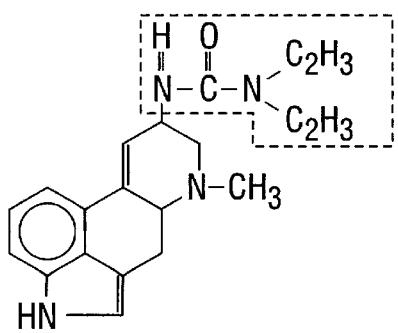

The term "dopamine agonist" also includes analogs of dopamine molecules which exhibit at least some biological activity in common with native human dopamine receptors. Exemplary analogs of dopamine include the ergolines and the aporphines as illustrated in FIG. 4, and other dopamine analogs having an agonist activity toward the dopamine receptor. In particular, the compositions disclosed herein are useful in the treatment of alcoholism and related compulsive disorders, especially in patients having the A1 allele of the DRD2 gene. The term "A1 allele" is meant to include either the A1/A1 or A1/A2 genotypes of the DRD2 gene.

2.7 PHARMACEUTICAL COMPOSITIONS

A further aspect of the invention are compositions comprising at least two dopamine agonists (which are specific for the DRD2 dopamine receptor) or opioidergics in a pharmaceutically-acceptable excipient. In a preferred embodiment at least one of the dopamine agonists is bromocriptine. The opioidergics may be selected from the group consisting of naloxone, naltrexone, naloxone methoiodide, naloxonazine, naltrindole, naltrindole isothiocyanate, naltriben, norbinaltorphimine, funaltrexamine, cyprodime, cyclozocine, diprenorphine, etazocine, levalorphan, metazocine, spiroindane, nalmefene, and nalorphine, or salts, analogs, or derivatives thereof Additionally, the composition may further comprise a serotonin reuptake inhibitor selected from the group consisting of fluoxetine, sertraline, paroxetine, fluvoxamine, venlafaxine, and nefazodone, or salts, analogs, or derivatives thereof A further aspect of the invention is a composition which comprises at least two dopamine agonists (which are specific for the DRD2 dopamine receptor) and one or more opioidergics in a pharmaceutically-acceptable excipient. In a preferred embodiment, at least one of the dopamine agonists is bromocroptine. The opioidergics may be selected from the group consisting of naloxone, naltrexone, naloxone methoiodide, naloxonazine, naltrindole, naltrindole isothiocyanate, naltriben, norbinaltorphimine, funaltrexamine, cyprodime, cyclozocine, diprenorphine, etazocine, levalorphan, metazocine, spiroindane, nalmefene, and nalorphine, or salts, analogs, or derivatives, thereof. The composition may further include one or more serotonin reuptake inhibitors, such as fluoxetine, sertraline, paroxetine, fluvoxamine, venlafaxine, nefazodone, or salts, analogs, or derivatives thereof In another aspect of the invention, there is provided a composition comprising at least two dopamine agonists, wherein both dopamine agonists are specific for the DRD2 dopamine receptor, one or more opioidergics, and a serotonin reuptake inhibitor in a pharmaceutically-acceptable excipient. In a preferred embodiment, at least one of the dopamine agonists is bromocroptine. The opioidergics may be selected from the group consisting of naloxone, naltrexone, naloxone methoiodide, naloxonazine, naltrindole, naltrindole isothiocyanate, naltriben, norbinaltorphimine, funaltrexamine, cyprodime, cyclozocine, diprenorphine, etazocine, levalorphan, metazocine, spiroindane, nalmefene, and nalorphine, or salts, analogs, or derivatives, thereof The composition may further include one or more serotonin reuptake inhibitors, such as fluoxetine, sertraline, paroxetine, fluvoxamine, venlafaxine, nefazodone, or salts, analogs, or derivatives thereof The pharmaceutical compositions disclosed herein may be orally administered, for example, with an inert diluent or with an assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithih, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral prophylaxis the polypeptide may be incorporated with excipients and used in the form of non-ingestible mouthwashes and dentfrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

The composition can be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

3. BRIEF DESCRIPTION OF THE DRAWINGS

The drawings form part of the present specification and are included to further demonstrate certain aspects of the present invention. The invention may be better understood by reference to one or more of these drawings in combination with the detailed description of specific embodiments presented herein.

FIG. 1. Craving scores in alcoholic subjects at 0, 3 and 6 weeks of the bromocriptine/placebo trial. The number of subjects in each group were BOR, 35; PLA, 17; A1, 18, A2, 34; BRO A1, 14; BRO A2, 21; PLA A1, 4; PLA A2, 13. Values represent means±SEM.

Figure 2:
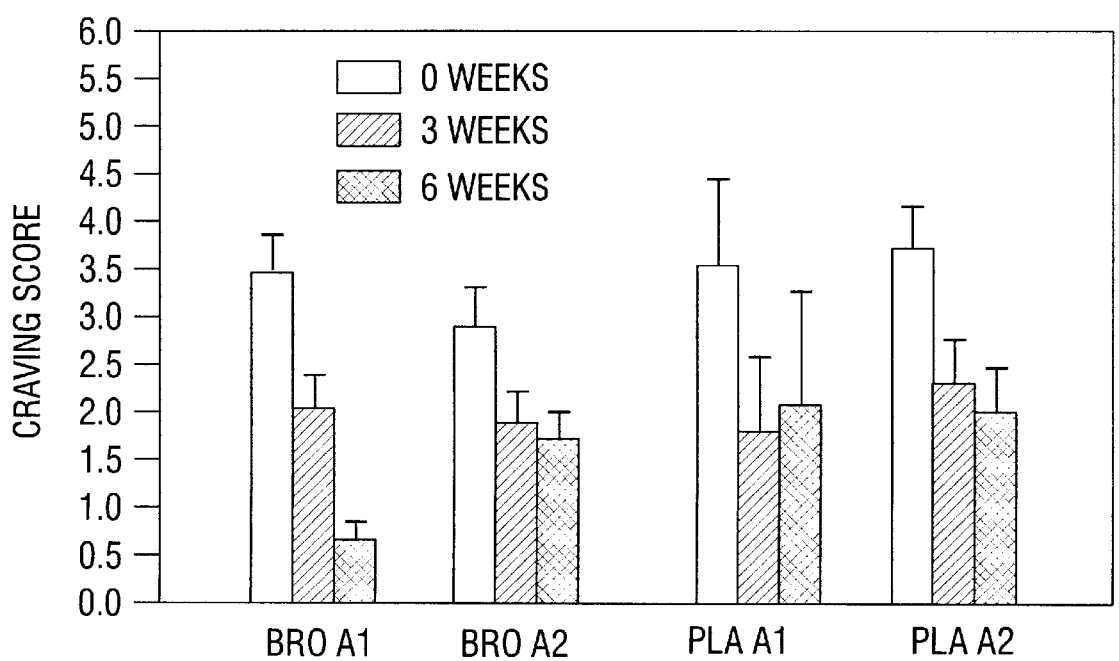

FIG. 2. Anxiety scores in alcoholic subjects at 0, 3 and 6 weeks of the bromocriptine/placebo trial. The number of subjects in each group is as for FIG. 1.

Figure 3A:
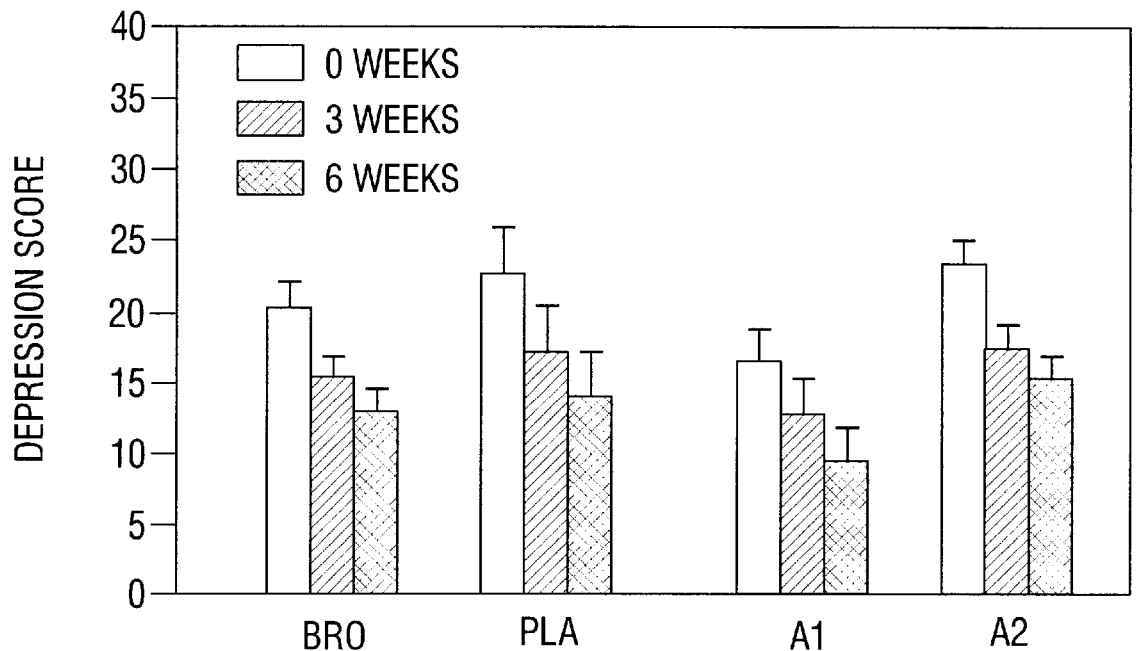
Figure 3B:
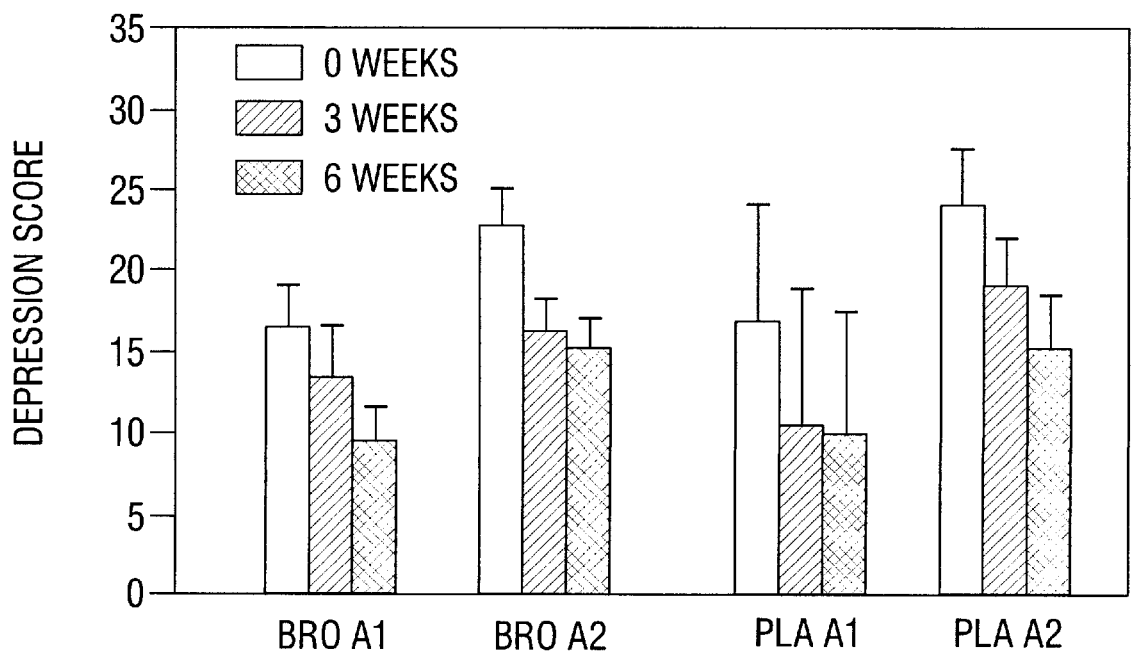

FIG. 3. Depression scores in alcoholic subjects at 0, 3 and 6 weeks of the bromocriptine/placebo trial. The number of subjects in each group is as for FIG. 1.

FIG. 4. Structural similarities between dopamine, apomorphine, and representative ergolines.

4. DESCRIPTION OF ILLUSTRATIVE EMBODIMENTS

The present invention represents a significant benefit to the field of alcoholism and an improvement of the state of the art in the field. By providing unique compositions and methods, the invention provides an effective and targeted pharmacological treatment for a certain severe molecular genetic type (DRD2 A1 allele) of alcoholics. Such an approach may also provide compositions and methods for the treatment of other drug dependencies which involve the dopaminergic system.

4.1 SOME ADVANTAGES OF THE INVENTION

The present invention represents a significant breakthrough in the medical arts by providing improved methods for the treatment of alcoholism in humans. For the first time, the inventor has demonstrated that the brain's "reward pathway" is turned off more quickly with opioidergic compounds such as naltrexone and naloxone in patients having the $D_2$ dopamine receptor A1 allele. These suprising results have explained, for the first time, a link between A1 allele determination and treatment using either dopamine antagonists opioidergic compounds. The results of these studies provide for improved treatment and recovery of patients with A1/A1 or A1/A2 DRD2 genotypes, by coupling DRD2 diagnosis methods with treatment using dopaminergic or opioidergic compounds.

The methods of the present invention generally involve obtaining a blood sample from a patient suspected of being an alcoholic, then genotyping the D2 receptor alleles. For those alcoholics with the genetic form of the disease (i.e. those who carry the A1 allele), a treatment regimen is then coupled to this diagnosis which provides the greatest improvement in alcoholism of such an A1-allele carrying subject. In one such treatment method, the treatment consists of administration of therapeutically-effective amounts of either a dopaminergic composition such as bromocriptine (e.g., in an amount of 2.5 mg given three times daily), or an opioidergic composition such as naloxone or naltrexone (e.g., in an amount of 50 mg daily). In one embodiment, the treatment method comprises administration of a single dopaminergic composition alone. Alternatively, a combination of one or more dopaminergic compounds may be administered either alone or in combination with one or more opioidergic compounds. In a further alternative, a single opioidergic compound (e.g., naloxone or naltrexone) may be administered to A1 allele patients.

4.2 ALCOHOL AND ALCOHOLISM

Alcohol is usually a reinforcing agent that produces pleasurable feelings in users. Neurochemical, pharmacological, physiological and behavioral studies suggest an important role for the mesolimbic dopamine (DA) system in the reinforcing effects (Koob, 1992). Alcohol increases extracellular DA levels in the nucleus accumbens (Imperato and Di Chiara, 1986; Weiss et al., 1993.), a brain reward area, and increases in a dose-dependent manner the firing rate of ventral tegmental DA neurons, indicating that the drug activates the mesoaccumbens DA system (Brodie et al., 1990.).

It has been known for a long time that alcoholism runs in families. The question of whether environment or heredity is the prime determinant for the development of alcoholism continues to receive extensive attention. However, in the past two decades, evidence derived from adoption and twin studies supports the likelihood of an important genetic component in alcoholism.

4.3 ALCOHOLIC TYPES

Evidence from clinical, experimental and genetic research indicates that there are at least two types of alcoholics. Jellinek (1960) emphasized the distinction between alcoholics who had persistent alcohol-seeking behaviors (that is, "inability to abstain entirely") and others who could abstain from alcohol for prolonged periods. More recently, Cloninger (1987), through empirical studies, found that alcohol-seeking behaviors, among other behaviors and personality traits, distinguish type 1 and type 2 alcoholics. Type 1, with necessary environmental provocative factors and hereditary background, is characterized by an ability to abstain. Type 2, a more severe form of alcoholism with necessary hereditary background, is characterized by an inability to abstain, irrespective of environmental provocative factors.

Various types of alcoholics have been described and heredity has been shown to be involved in some of these types. An important role of the mesolimbic dopamine system has been suggested in the reinforcing effects of alcohol and recent molecular genetic studies are implicating the gene for the $D_2$ dopamine receptor (DRD2) in alcoholism.

4.4 ALLELES OF THE DRD2 GENE

A molecular genetic component involved in alcoholism was first shown when an association of the minor allele (A1) of the gene for the $D_2$ dopamine receptor (DRD2) was found with this disorder (Blum et al., 1990). Subsequently, a large number of studies, both in the United States and abroad, have examined the role of the DRD2 gene in alcoholism. Several meta-analyses of these extant studies show an association of the A1 allele with alcoholism (Cloninger, 1991; Noble, 1993; Prato et al., 1993; Uhl et al., 1993; Gorwood et al., 1994; Cook and Gurling, 1994) (one has not Gelernter et al., 1993, however, see Noble and Blum, 1993). Moreover, the minor DRD2 allele has also been found to be associated with various substance use disorders including polysubstance abuse (Comings et al., 1993; Smith et al., 1992; Comings et al., 1994), cocaine (Noble et al., 1993) and nicotine (Noble et al., 1994d) dependence and obesity (Noble et al., 1994c). Furthermore, reduced dopaminergic function has been observed in alcoholics (Balldin et al., 1992; Balldin et al., 1993) and in subjects carrying the DRD2 A1 allele (Noble et al., 1991; Noble et al., 1994e; Berman and Noble, 1995).

If alcoholics with the DRD2 A1 allele have reduced dopaminergic function, treatment with a dopaminergic agonist might have a more salutary effect on them than on alcoholics who carry the major allele (A2). This question is addressed in this report by Lawford, Noble and colleagues (1995) studying the effects of bromocriptine, a DRD2 agonist, or placebo on changes in behavioral characteristics (craving, anxiety and depression) and on the attrition rates of hospitalized A1 (A1/A1 and A1/A2 genotypes) and A2 (A2/A2 genotype only) alcoholics. The results showed the greatest improvement was observed in A1 alcoholics (vide infra).

Alcoholism is recognized as a heterogeneous disorder, with hereditary and environmental components as contributors to its development. Unfortunately, therapeutic approaches to mitigate the high recidivism rate of alcoholics have produced discouraging or at best mixed results. However, if alcoholics with a hereditary component can be effectively treated with specific pharmacological agents, such a pharmacogenetic approach could have important implications for clinical medicine.

U.S. Pat. Nos. 5,210,016 and 5,500,343 demonstrated the pioneering discovery of allelic association with compulsive disorder and provides a method for detecting on a molecular basis a genetic potential susceptibility to compulsive disorders such as alcoholism. In particular, the detection of certain alleles associated with the genes encoding the human dopamine $D_2$ receptor protein is an indication of a genetic potential susceptibility to compulsive disorder. Methods were provided for the detection of a genetic potential susceptibility to an impulsive, addictive, or compulsive disorder by detecting the presence of a human dopamine $D_2$ receptor gene A1 or B1 alleles.

The dopamine receptor has been implicated as a prime target site in cells of the brain reward system (Liljequist, 1978; Newlin et al., 1981; Mereu et al., 1984; Stein and Belluzi, 1986; Govoni et al., 1986; Valverius et al., 1989; Fadda et al., 1989). Five major dopaminergic systems in the human brain have been identified ($D_1$–$D_5$). The nigrostriatal is involved in the initiation and execution of movement; the tuberoinfundibular is responsible for the regulation of peptide secretion from the pituitary; and the mesolimbic tract controls emotional stability and affect. Mediating these effects of dopamine are two receptor subtypes, $D_1$ and $D_2$ (also designated as D1 and D2), each of which is coupled to different second messenger systems. The $D_1$ receptor has been implicated in the sleep disorder, insomnia. Most recently, a $D_3$ receptor has been found (Sokoloff et al., 1990) and is also implicated in limbic system function.

Important clinically relevant studies on the pharmacology of $D_2$ receptors indicated that antipsychotic drugs display high affinities for the receptor. Other work suggested that the $D_2$ receptor is involved in movement disorders, i.e. Parkinson's disease and tardive dyskinesia, tumors of the pituitary, and compulsive disease.

Recent studies (Neiswanger et al., *Am. J. Med. Genet.* 60:267–271; 60:272–275, 1995) have confirmed the association of the DRD2 TaqI A1 allele and compulsive disorders such as alcoholism. Linkage and association studies were performed using alcoholic men from high-density families largely uncontaminated by other psychopathology, and female alcoholics who also suffered from secondary drug dependence. Neiswanger et al, concluded "the original positive association of the TaqI A1 allele to alcoholism (Blum et al., 1990) has been replicated several times (Blum et al., 1991; Parsian et al., 1991; Comings et al., 1992; Amadeo et al., 1993; Neiswanger et al., 1995). With careful construction of control groups, e.g., the use of both carefully diagnosed random controls and 'super-normal' controls, population-based association studies also have the potential to help detect genetic risk factors which might go unidentified using other means. Hence it is advantageous to use the lessons of the DRD2 controversy to adapt this experimental approach to the specific challenges presented by psychiatric genetics, rather than dismiss it prematurely."

4.5 DOPAMINE AGONISTS IN THE TREATMENT OF ALCOHOLISM

Dopaminergic agents have been used to study alcohol-related behaviors in animals. DRD2 agonists (e.g., bromocriptine and quinpirole) have been shown to decrease alcohol intake (McBride et al., 1990; Weiss et al., 1990; Dyr et al., 1993; Rassnick et al., 1993). On the other hand, antagonists of this receptor (e.g., sulpiride and spiperone) cause increases in alcohol intake (Dyr et al., 1993; Levy et al., 1991). However, results with antagonists have not been consistent.

Animal genetic models of alcoholism also implicate the dopaminergic system in this disorder. In alcohol-naive alcohol-preferring and non-alcohol-preferring rat strains, a decreased number of DRD2 receptors has been found in the brains of the alcohol-preferring animals (Stefanini et al., 1992; McBride et al., 1993).

Studies of humans provide further support to a connection between alcoholism and the dopaminergic system. Neuroendocrine evidence of reduced DRD2 receptor sensitivity has been found in alcoholics after a few months or after several years of alcohol abstinence (McBride et al., 1990; Balldin, 1993). It is suggested that this reduced receptor function is a trait marker for this disorder. However, the possibility that the reduced dopaminergic function has been acquired after earlier periods of heavy alcohol consumption cannot be ruled out. Moreover, as indicated earlier, molecular genetic studies are implicating the DRD2 gene in alcoholism. Specifically, the A1 allele of this gene was found to be associated with alcoholism, particularly the severe type of this disorder. Furthermore, in a recent study (Lawford, Noble and colleagues, 1995), the inventor has determined the prevalence of the A1 allele in a sample of Australian Caucasian alcoholics as well as non-alcoholics (n=93), the prevalence of the A1 allele was 44.1% and in the non-alcoholics (n=34), the prevalence of this allele was 14.7%; a difference that is statistically significant ($\chi^2$=8.07, P<0.005).

No mutation has been found in the coding exons of the DRD2 gene in alcoholism (or in schizophrenia) to support a structural change in the DRD2 gene (Gejman et al., 1994). However, evidence for diminished DRD2 receptor function is provided by decreased brain DRD2 receptor numbers (Noble et al., 1991) and indirectly, by prolonged P300 latency (Noble et al., 1994e) (a brain event-related potential) and reduced visuospatial functioning (Berman and Noble, 1995) in subjects carrying the DRD2 A1 allele. It is suggested that the most likely explanation for the relationship between increased expression of symptom severity and the prevalence of the A1 allele, is that a mutation in linkage disequilibrium with TaqI A is associated with functional decrease in DRD2 gene expression (Comings et al., 1993).

Clinical studies of dopamine agonists, such as bromocriptine and apomorphine, have, in general, shown their efficacy in the treatment of alcoholism and its associated problems (Carlsson et al., 1977; Borg and Weinholdt, 1980; Morgan et al., 1980; Feldman, 1983), although some of these studies did not demonstrate rigorous methodologies. However, Borg (1983), using Norwegian outpatient alcoholics, conducted one of the first double-blind BRO/PLA trials. Craving scores decreased in both the BRO and PLA groups during the 6-month trial. Greater decreased scores were first evident in the BRO group after one month of treatment. At 3 and 6 months, craving scores continued to decrease in the BRO group, while they remained essentially unchanged in the PLA group. Moreover, the overall improvement in the number and duration of drinking episodes, in psychological states, and in social functioning was greater in the BRO group. Benefits from BRO treatment have also been shown in a recent double-blind 2-month BRO/PLA trial on Canadian ambulatory alcoholics (Dongier et al., 1991).

4.6 DOPAMINE $D_2$ RECEPTOR DENSITIES AND DRD2 ALLELES

Dopamine $D_2$ receptors densities are lower in brain tissue obtained from patients carrying the A1, B1, and $DRD2^{In6-Ex7}$ haplotype I alleles of the DRD2 gene (Flanagan et al., 1992; Noble et al., 1991). Similar reduced DRD2 densities have also been found in alcohol preferring rodents compared to alcohol-non-preferring inbred animals (McBride et al., 1993; Stefanini, 1992). Moreover, $D_2$ receptor agonists significantly reduce alcohol intake in high alcohol preferring rats, whereas $D_2$ receptor antagonists increase alcohol intake in these inbred rodents (Dyr et al., 1993).

5. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

5.1 Example 1

BROMOCRIPTINE TREATMENT OF DRD2 A1 ALCOHOLICS

This example illustrates the effects of the dopamine agonist, bromocriptine, on craving and anxiety in alcoholic patients. In a double-blind study (Lawford, Noble and colleagues, 1995), bromocriptine, a DRD2 agonist, or placebo was administered to alcoholics with either the A1 (A1/A1 and A1/A2 genotypes) or only the A2 (A2/A2 genotype) allele of the DRD2 gene. The greatest improvement in craving and anxiety occurred in the bromocriptine-treated A1 alcoholics and attrition was highest in the placebo-treated A1 alcoholics. Significant differences in decreased craving and anxiety were found between the two key comparative groups (BRO A1 and BRO A2). The study was conducted in the therapeutic but controlled setting of a hospital, thus obviating the necessity to assess drinking behaviors.

5.1.1 SUBJECTS

All subjects were inpatients at the Wolston Park Hospital, Wacol, Queensland, Australia. eighty-three chronic alcoholics met Diagnostic and Statistical Manual of Mental Disorders (DSM-III-R) criteria for alcohol dependence and had no other major psychiatric disorder, Alcohol Amnestic disorder, or significant cognitive impairment were included in the trial. The average age of the sample (±SEM) was 43.7 (±1.3) years. Most of the alcoholics were males (m=78, f=5) and all of the alcoholics were of European Caucasian descent. None of the alcoholics were morbidly obese. All patients had a history of multiple admissions for treatment of their alcoholism and many had medical problems associated with their disorder. All had been fully detoxified before inclusion in the study, and no patient was allowed an overnight or a weekend leave from the hospital.

Subjects were randomly allocated, in a double-blind manner (and without knowledge of the DRD2 genotype), to administration of either bromocriptine (2.5 mg, three times a day) or a placebo (vitamin C, 250 mg, three times a day)

for a 6-week trial. Because of the possibility of increased attrition due to the potential side effects of bromocriptine, a larger proportion of subjects were assigned to the bromocriptine (n=52) than the placebo (n=31) condition. Bromocriptine or placebo (identical in appearance) was administered to the patients in the presence of a staff member. Institutional approval was obtained to conduct this trial, and all patients gave their written consent. Patients were informed of the nature and consequences of the study and were told that they could leave the trial at will and without prejudice.

5.1.2 ANALYSES

On entry into the study, 10 ml of blood was taken from each patient. Genomic DNA was extracted by standard procedures and subsequently used as a template for PCR™ determination of TaqI A DRD2 alleles (Noble, 1994b). The Borg Craving Scale (Borg, 1983), the Spielberger State Anxiety Inventory (Spielberger, 1983) and the Beck Depression Inventory (Beck, 1978) were administered, under supervision, at 0 week, 3 weeks and 6 weeks of the trial.

5.1.3 STATISTICS

Separate two-way analyses of variance (ANOVAs) were used on the difference scores for each of the two time intervals (0–3, 3–6 weeks) to examine the effects of treatment (BRO, PLA) and allele (A1, A2) and treatment×allele interaction on changes in the craving, anxiety and depression scores. Preplanned specific group contrasts were conducted based on the ANOVAs. Furthermore, attrition was also examined in the four treatment/allele groups between the 0–3 weeks and 3–6 weeks of the trial using $\chi^2$ analysis. A P value of <0.05 was considered to be statistically significant. The more conservative two-tailed rather than one-tailed statistic was used even though it was hypothesized that the greatest behavioral reduction scores in the four treatment/allele groups (BRO A1, BRO A2, PLA A1 and PLA A2) would occur in the BRO A1 group.

5.1.4 RESULTS

Of the 83 alcoholics who initially enrolled in this 6-week double-blind trial to compare bromocriptine (BRO) with placebo (PLA), 52 (62.7%) complied with all aspects of the experimental design and completed the entire study. Only two of the initial volunteers reported significant side effects (one taking BRO experienced postual hypotension and another taking PLA had persistent nausea), necessitating their withdrawal from the trial. The remaining 'non-completers' left the hospital against medical advice. Below, the behavioral data (craving, anxiety, depression) and their analyses for the 52 alcoholics who completed the study are presented as well as the attrition rate of the 83 initial patients who entered the trial.

Since the dose of BRO (7.5 mg daily) used in this study has been previously shown not to exert its effect on craving until after three weeks of treatment (Borg, 1983), craving, anxiety and depression scores were analyzed over two time intervals: 0 (entry) to 3 weeks and 3 to 6 weeks (end of the trial). The following analyses of changes in the three behavioral measures were conducted: (1) between the two treatment groups (BRO, PLA); (2) between the two allele groups A1 (consisting of A1/A1 and A1/A2 genotypes) and A2 (consisting of A2/A2 genotype only), and (3) among the four treatment/allele groups (BRO A1, BRO A2, PLA A1 and PLA A2). Furthermore, differences in these three behavioral measures were compared in the two treatment and the two allele groups at entry. Finally, comparisons were made among the four treatment/allele groups of attrition rate during the 6-week trial.

Given previous observations that alcoholics carrying the A1 allele have the more severe form of the disorder (Noble, 1993; Uhl et al., 1993.), and in view of studies suggesting reduced dopaminergic function in subjects who carry the A1 allele (Noble et al., 1991; Noble et al., 1994e; Berman and Noble, 1995), the inventor hypothesized that the greatest decrease in craving, anxiety and depression scores in the four treatment/allele groups would occur in alcoholics carrying the A1 allele who are treated with BRO.

The changes in craving scores in this sample of alcoholics are presented in FIG. 1. The changes in the two treatment (BRO, PLA) and the two allele (A1, A2) groups are shown in FIG. 1A. The changes in the four treatment/allele groups (BRO A1, BRO A2, PLA A1, PLA A2) are shown in FIG. 1B. No significant treatment or allele effect on craving or treatment×allele interaction for craving was found in the interval of 0–3 weeks. However, in the interval of 3–6 weeks a significant treatment effect was obtained (P=0.027), with craving scores decreasing by 34.0% in the BRO group compared with 8.5% in the PLA group (FIG. 1A). Furthermore, during the interval of 3–6 weeks, there was a significant treatment×allele interaction (P=0.011). Specifically, the decrease in craving scores was greatest in the BRO A1 (68.0%) group compared with the BRO A2 (10.2%), the PLA A1 (−14.3%) and the PLA A2 (13.9%) groups (FIG. 1B). Preplanned comparison showed this decrease to be more than sixfold greater in the BRO A1 compared with the other three treatment/allele groups combined (P=0.003).

The changes in anxiety scores for the two treatment, two allele and four treatment/allele groups are shown in FIG. 2. In the interval of 0–3 weeks, there was no significant treatment or allele effect or treatment×allele interaction. However, in the four treatment/allele groups, the decrease in anxiety scores was greatest in the BRO A1 (14.8%) group compared with the BRO A2 (−0.4%), the PLA A1 (−0.8%) and the PLA A2 (−6.6%) groups (FIG. 2B). Preplanned comparison showed the decrease in anxiety, like the craving scores, was significantly greater in the BRO A1 group compared with the BRO A2 group (P=0.013). Furthermore, the decrease in anxiety scores was also significantly greater in the BRO A1 group compared with the other three treatment/allele groups combined (P=0.004). However, in the interval of 3–6 weeks, changes in anxiety scores were not significantly differentiated among the four treatment allele groups.

Changes in depression scores in the two treatment, two allele and four treatment/allele groups are shown in FIG. 3. Unlike craving and anxiety, decreases in depression scores were not differentially associated with any specific treatment or allele group or treatment/allele group.

Figure 2A:
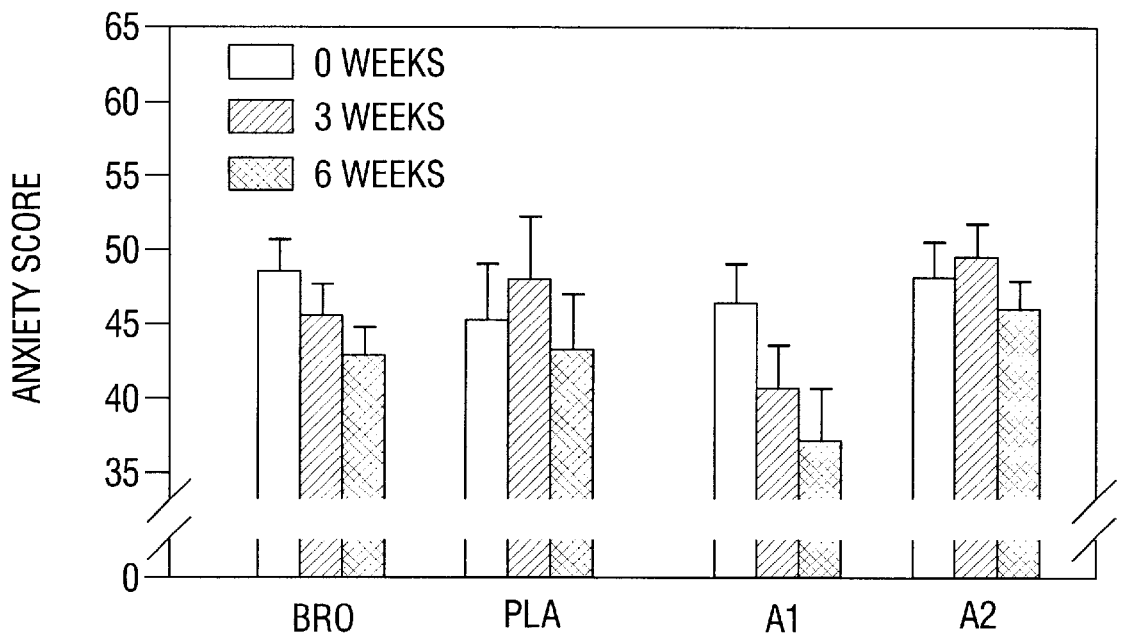
Figure 2B:
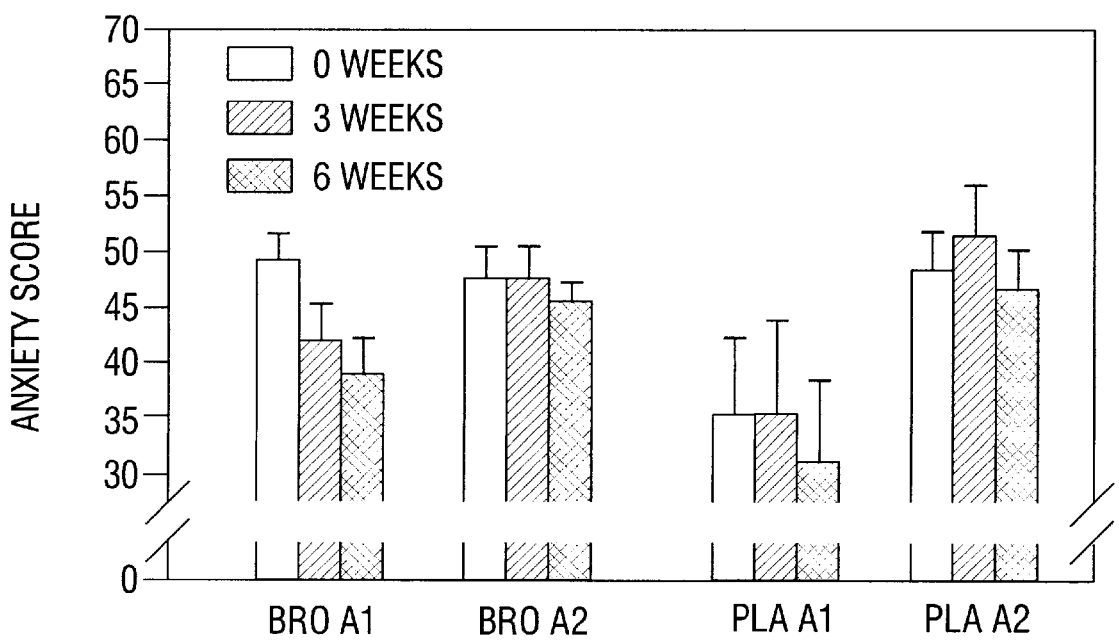

To determine whether at entry the three behavioral measures were different in the alcoholics who were assigned to the BRO or the PLA group, comparisons of craving, anxiety and depression scores were made between these two groups (FIG. 1A, FIG. 2A and FIG. 3A). None of these behavioral scores were significantly different in the two treatment groups. Similarly, there were no significant differences between the A1 and A2 alcoholics in craving, anxiety and depression scores at entry into the trial.

In sum, in the four treatment/allele groups studied, alcoholics who carried the A1 allele and had received BRO showed the greatest reductions in craving and anxiety scores, with the latter preceding the former in time. Decreased depression scores, on the other hand, were not significantly differentiated among these four groups.

The attrition rate of A1 and A2 allele alcoholics treated with BRO and PLA are presented in Table 1. Data analysis for the interval of 0–3 weeks showed no significant difference between the BRO- and the PLA-treated group for the ratio of patients who dropped out compared with those who remained in the trial.

TABLE 1

Attrition Rate of A1 and A2 Allele Alcoholics Treated With Bromocriptine or Placebo at 0,3 and 6 Weeks of the Trial

| Weeks in treatment | Bromo A1 | Bromo A2 | Placebo A1 | Placebo A2 |
|---|---|---|---|---|
| | (n) | (n) | (n) | (n) |
| 0 | 19 | 33 | 12 | 19 |
| 3 | 17 | 26 | 11 | 17 |
| 6 | 14 | 21 | 4 | 13 |

There was also no significant difference in this measure among the four treatnentlallele groups. When the interval of 3–6 weeks was examined, the attrition to retention ratio of the patients was lower for the BRO group (8/35) than the PLA group (11/17). However, the difference between these two groups was not significant ($\chi^2=2.72$, P=0.099). When the four treatment/allele groups were exarnined, the attrition to retention ratio increased progressively in the BRO A1 (3/14), BRO A2 (5/21), PLA A2 (4/13) and PLA A1 (7/4) groups in that order. Moreover, there was a significant difference among these four groups ($\chi^2=9.20$, P=0.027). Post hoc analysis showed the attrition to retention ratio was significantly higher in the PLA A1 than in the BRO A1 group ($\chi^2=4.31$, P=0.038). Finally, this ratio in the PLA A1 group was also significantly higher than in the other three treatment allele groups combined ($\chi^2=6.94$, P=0.008).

5.1.5 DRD2 GENOTYPES AND BROMOCRIPTINE TREATMENT

Despite the existence of different types of alcoholics, pharmacological studies of alcoholism have rarely taken into consideration alcoholic types on treatment outcome. In this double-blind BRO/PLA trial, it has been ascertained that the effect of treatment on alcoholics carrying either the DRD2 A1 or A2 allele. It is hypothesized that alcoholics with the A1 allele, having low $D_2$ dopaminergic function, would experience the greatest benefit from BRO treatment compared with the other three groups (BRO A2, PLA A1, PLA A2). The results of the study support this hypothesis in showing that in the four treatment/allele groups, the greatest decreases in craving and anxiety occurred in the BRO A1 alcoholics.

Craving, an obsessive desire for alcohol, is a common experience in alcoholics and has been viewed as an important determinant of relapse. In this study, the effect of BRO in reducing craving was manifested after about three weeks of treatment, a finding also observed by Borg (1983). This reduction was significantly greater in the BRO A1 group than its key comparative BRO A2 group, and also significantly greater when compared with the other three treatment/allele groups combined. Likewise, the reduction in anxiety in the BRO A1 group was significantly greater when compared either with the BRO A2 group or with the other three treatment/allele groups combined. However, the effect on anxiety in the BRO A1 group occurred before (0–3 weeks) the effect on craving (3–6 weeks). Whether there is a causal connection between the reduction in anxiety and the reduction in craving in the BRO A1 group remains to be determined.

Depression is also a common experience in alcoholics, but with abstinence, a rapid resolution of depression usually occurs in hospitalized alcoholics. In this sample of alcoholics, a decrease in depression was also found in the four BRO/PLA groups during the 6 weeks of hospitalization. However, unlike craving and anxiety, the decrease in depression was not significantly differentiated among these four groups.

A number of studies have shown substantial 28–80% attrition rates of alcoholics within the first month of treatment, and attempts to reduce this have been largely unsuccessful. In a study of alcoholics, an attrition rate within this range (37.3%) was found during the six weeks of hospitalization. No significant differences in attrition to retention ratios were found among the four BRO/PLA groups during the initial three weeks of hospitalization. On the other hand, in the third to sixth weeks of the trial, the period when BRO began to exert its effects on craving in A1 allelic alcoholics, significant differences were observed among the four treatment/allele groups. This attrition to retention ratio was significantly higher in the PLA A1 group than the BRO A1 group. It is possible that the BRO-induced reduction in craving will result in patients being more receptive to rehabilitative efforts. However, the data suggest that BRO must be administered for more than three weeks before its salutary effects are manifested, and that it is effective only in alcoholics carrying the A1 allele.

5.2 Example 2

[$^3$H]NALOXONE BINDING IN THE HUMAN BRAIN

The interconnections between the opioidergic and dopaminergic systems and their mediation in the effects of ethanol take on added significance with the demonstration of an association of the minor (A1) allele of the $D_2$ dopamine receptor (DRD2) gene with alcoholism (for reviews, see Noble, 1993; Uhl et al., 1993). Moreover, reduced number of $D_2$ dopamine receptors have been shown not only in the caudate nucleus of DRD2 A1 subjects (Noble et al., 1991), but diminished brain dopaminergic function has also been found in these subjects when compared to those who do not have this allele (Berman and Noble, 1995; Noble et al., 1994a). In the present study, the inventor describes differences in the binding of the opiate receptor antagonist naloxone to various brain regions of human subjects based on the presence or absence of alcoholism as well as whether or not they carry the DRD2 A1 allele.

5.2.1 MATERIALS AND METHODS

Brains of 24 alcoholic and 31 nonalcoholic subjects were obtained from the National Neurological Research Specimen Bank at the Veterans Affairs Medical Center, West Los Angeles, Calif. The frontal gray cortex, caudate nucleus, amygdala, hippocampus and cerebellar cortex were removed from the brain at autopsy and immediately frozen at –70° C. until used. In certain cases, some of the brain regions noted above were not available from all of the subjects. All subjects were of Caucasian descent. The alcoholic subjects included 19 males and 5 females, while there were 24 male and 7 female nonalcoholic subjects ($\chi^2=0.03$, p=0.86). The ages (mean±SEM) of the alcoholics and nonalcoholics were 49.0±3.0 years and 51.5±2.6 years, respectively (p=0.44). The autolysis times (mean±SEM) of the alcoholic and nonalcoholic samples were 24.7±2.0 hours and 22.5±1.8 hours, respectively (p=0.71). Diagnosis of alcoholism was made independently by two trained psychiatrists using DSM-III-R (1987) criteria of alcohol dependence and abuse through examination of medical and autopsy records, interviews of treatment center personnel and relatives, and alcohol consumption data. These two assessments were 100% concordant in diagnosing alcoholic and nonalcoholic subjects. Examination of medical records and/or results of analysis of body fluids at autopsy did not indicate that any of the subjects had used neuroleptic agents. The cause of death of the alcoholics included Laennec's cirrhosis, anasarca, cardiopulmonary-renal failure, ruptured esophageal varices, among others. The cause of death of the nonalcoholics included cancer, myocardial infarction, stroke, accidents, homicide and suicide. Informed consent was obtained from next of kin to perform this study.

Genomic DNA was extracted from the frontal gray cortex using standard techniques and subsequently used as template for determination of the TaqI A DRD2 alleles by the polymerase chain reaction (Saiki et al., 1988). The amplification of DNA was carried out using a Perkin-Elmer GeneAmp 9600 thermocycler (Perkin-Elmer, Foster City, Calif.) as described previously (Noble et al., 1994b). Approximately 500 ng of amplified DNA was digested with 5 U of TaqI restriction enzyme (GIBCO/BRL, Grand Island, N.Y.) at 65° C. overnight. The resulting products were analyzed by gel electrophoresis in a 2.5% agarose gel containing ethidium bromide and visualized under ultraviolet light. The A1/A2 genotype is revealed by three fragments: 310 bp, 180 bp and 130 bp; the A2/A2 genotype is indicated by two fragments: 180 bp and 130 bp; and the A1/A1 genotype is shown by the uncleaved 310 bp fragment. Subjects homozygous (A1/A1) and heterozygous (A1/A2) for the A1 DRD2 allele are referred to as A1$^+$ subjects, while those homozygous for the A2 allele (A2/A2) are referred to as A1$^-$ subjects.

[$^3$H]Naloxone binding was measured by a modification of established procedures (Simantov et al., 1978). In 35 ml of 50 mM Tris-HCl, pH 7.7, 50 mg of brain tissue was homogenized and centrifnged at 25,000×g for 15 min. The resulting pellet was resuspended in 35 ml of buffer and recentrifnged. The pellet was finally resuspended in 5 mnl of Tris-HCl, pH 7.7. Nonsaturable binding was determined by the addition of 2.5 $\mu$M nonradioactive naloxone. Total binding was determined in the absence of excess nonradioactive naloxone. The final assay volume was 2 ml. Binding was initiated by the addition of tissue suspension (250 $\mu$g protein), and the samples were incubated at 25° C. for 40 min. The samples were then rapidly filtered through GB/F glass fiber filters with a Brandel cell harvester and the filters were washed twice with 4 ml of ice-cold Tris-HCl, pH 7.7. Radioactivity on the filters was determined by liquid scintillation counting. protein was determined by the method of Lowry et al. (1951). Specific binding was determined as the difference between total binding and nonsaturable binding and is expressed as fmole [$^3$H]naloxone bound per mg protein.

5.2.2 RESULTS

Examination of the frequency distributions of [$^3$H] naloxone binding for the samples showed skewness and kurtosis values to be outside the limits of ±1 in each of the brain regions. Therefore, square root transformation of the variables was performed to bring the values within acceptable limits for these two measures. Mean differences in [$^3$H]naloxone binding between alcoholic and nonalcoholic groups and between groups with or without the A1 allele were tested using two-factor analysis of covariance (ANCOVA) to determine the statistical significance of the main effect of allele and alcoholism, and the possible interactions between allele and alcoholism. Linear correlations determined that for the hippocampus, [$^3$H]naloxone binding was dependent on age (P=0.044) and for the amygdala it was dependent on autolysis time (p=0.004). In addition, it was found that the slopes were not significantly different between the alcoholic and nonalcoholic groups and between the two allele groups. Therefore, for the hippocampus and amygdala, age and autolysis time were respectively used as covariates. There was no correlation of either age or autolysis time with [$^3$H]naloxone binding in the frontal cortex, caudate nucleus, or the cerebellum, so consequently, age and autolysis time were not used as covariates with these regions. Where significant ANCOVA results were obtained, Student's t-test was used to compare group differences. A p value of 0.05 or less was considered statistically significant.

Table 2 shows, in the nonalcoholic brains, the highest and lowest [$^3$H]naloxone binding is found in the amygdala and the cerebellum, respectively, with the other brain regions having intermediate values. This relative distribution of $\mu$ receptor binding has also been previously found in brain regions of humans (Kuhar et al., 1973; Pfeiffer et al., 1982). When the samples are examined on the basis of the presence or absence of the A1 allele, [$^3$H]naloxone binding is higher in all brain regions of the A1$^-$ allele compared to the A1$^+$ subjects. ANCOVA of the two-factor interaction shows the following. The effect of alcoholism on [$^3$H]naloxone binding is significant only in the frontal cortex (p=0.013). Group comparisons (Table 3) show binding was significantly higher in A1$^-$ alcoholics compared to A1$^+$ nonalcoholics (p=0.001). When classification of the subjects is based on the presence or absence of the A1 allele, there is a significant difference only in the caudate nucleus (p=0.008). Group comparisons (Table 3) show binding is significantly higher in A1$^-$ allele alcoholics when compared to either A1$^+$ alcoholics (p=0.001) or A1$^+$ allele nonalcoholics (p=0.029). No significant alcoholism×allele interactions are found in [$^3$H]naloxone binding in any of the brain regions examined.

Using tissue obtained post mortem, the present study shows that in various regions of the brain, particularly in the frontal cortex, [$^3$H]naloxone binding is higher in alcoholic than nonalcoholic subjects. Previous opiate receptor binding studies have shown that chronic ethanol exposure enhanced $\delta$ opiate binding in the brain of rats (Lucchi et al., 1985) and mice (Hynes et al., 1983) and in cultured cells of neural origin (Charness et al., 1986). Chronic ethanol ingestion also produced increases in the binding capacity of [$^3$H][D-Ala$^2$,-D-Leu$^5$] enkephalin, [$^3$H]dihydromorphine and [$^3$H] naloxone (Gianoulakis, 1989). While naloxone, at low concentration (0.4 nM) is primarily considered to be a $\mu$ receptor antagonist (Chang et al., 1981), at high concentration, it can also bind to $\delta$ receptors (Chang and Cuatrecasas, 1979). Thus, it is possible that the enhanced [$^3$H]naloxone binding observed with the naloxone concentration used herein (1.15 nM) may reflect binding to $\delta$ in addition to $\mu$ opiate receptors.

TABLE 2

[$^3$H]Naloxone Binding in Brain Regions of Alcoholics and Nonalcoholics
and Subjects with and without the DRD2 A1 Allele

| Brain Region | Alcoholics | | Nonalcoholics | | A1$^+$ Subjects | | A1$^-$ Subjects | |
|---|---|---|---|---|---|---|---|---|
| | n | Mean ± SEM | n | Mean ± SEM | n | Mean ± SEM | n | Mean ± SEM |
| Frontal Cortex[a] | 24 | 65.5 ± 5.0 | 31 | 50.3 ± 4.5 | 20 | 55.7 ± 6.5 | 35 | 57.7 ± 4.1 |
| Caudate Nucleus[b] | 23 | 39.4 ± 3.6 | 30 | 38.6 ± 3.1 | 19 | 30.9 ± 2.4 | 34 | 43.4 ± 3.1 |
| Amygdala | 18 | 61.4 ± 8.5 | 24 | 56.8 ± 6.3 | 17 | 52.7 ± 6.8 | 25 | 62.9 ± 7.2 |
| Hippocampus | 22 | 43.3 ± 5.7 | 24 | 36.3 ± 6.1 | 16 | 33.6 ± 5.8 | 30 | 42.9 ± 5.5 |
| Cerebellum | 24 | 38.2 ± 6.0 | 29 | 27.6 ± 2.8 | 20 | 30.3 ± 6.7 | 33 | 33.7 ± 3.2 |

A1$^+$ subjects include those who carry either the A1/A1 or A1/A2 genotype. A1$^-$ subjects include those who carry only the A2/A2 genotype. Binding of [$^3$H]naloxone was measured as described in the text and represents fmole [$^3$H]naloxone bound per mg protein of n samples (mean ± SEM).
[a]ANCOVA of the two factor of alcoholism and DRD2 allele shows a significant alcoholism effect in the frontal cortex (p = 0.013).
[b]ANCOVA of the two factor of alcoholism and DRD2 allele shows a significant DRD2 allele effect in the caudate nucleus (p = 0.008).

TABLE 3

[$^3$H]Naloxone Binding in Brain Regions of Alcoholics and Nonalcoholics
With or Without the DRD2 A1 Allele

| Brain Region | A1$^+$ Alcoholics | | A1$^+$ Nonalcoholics | | A1$^-$ Alcoholics | | A1$^-$ Nonalcoholics | |
|---|---|---|---|---|---|---|---|---|
| | n | Mean ± SEM | n | Mean ± SEM | n | Mean ± SEM | n | Mean ± SEM |
| Frontal Cortex[a] | 11 | 67.8 ± 3.8 | 24 | 53.1 ± 5.5 | 13 | 63.6 ± 8.8 | 7 | 41.0 ± 6.2 |
| Caudate Nucleus[b] | 11 | 49.9 ± 5.6 | 23 | 40.4 ± 3.7 | 12 | 29.9 ± 2.3 | 7 | 32.7 ± 4.9 |
| Amygdala | 8 | 67.8 ± 13.8 | 17 | 60.6 ± 8.6 | 10 | 26.3 ± 11.1 | 7 | 47.5 ± 5.3 |
| Hippocampus | 10 | 55.0 ± 8.5 | 20 | 36.9 ± 6.9 | 12 | 33.6 ± 6.7 | 4 | 33.7 ± 13.1 |
| Cerebellum | 11 | 45.1 ± 5.4 | 22 | 28.0 ± 3.3 | 13 | 32.4 ± 10.1 | 7 | 26.4 ± 5.4 |

[a]A1$^-$ alcoholics vs. A1$^+$ nonalcoholics, p = 0.001.
[b]A1$^-$ alcoholics vs. A1$^+$ nonalcoholics, p = 0.029; A1$^-$ alcoholics vs. A1$^+$ alcoholics, p = 0.001.

It has been previously shown that chronic ethanol administration to animals produced a significant decrease in the levels of opiate peptides in various brain regions (Gianoulakis, 1983; Seizinger et al., 1983). Diminished enkephalin release has also been demonstrated in rat striatal slices following chronic ethanol consumption (Lucchi et al., 1985). these findings suggest that chronic ethanol exposure diminishes both the levels and release of endogenous opiate peptides in the brain. It is possible that the enhanced opiate receptor binding observed in the present study of alcoholics may be a compensatory up-regulation of opiate receptors due to ethanol-induced diminished opiate input. This view is supported by work showing that pharmacological blockade of opiate receptors by the chronic administration of the opiate antagonist naltrexone in rates resulted in a marked increase in the number of both δ and μ opiate receptors in the brain (Tempel et al., 1985).

An interesting observation in this investigation is the decreased [$^3$H]naloxone binding, particularly in the caudate nucleus, of subjects with the A1$^+$ allele, regardless of alcoholism status. This finding takes on added significance in that the caudate nucleus has one of the highest densities of D$_2$ dopamine receptors in the human brain (Kessler et al., 1993), and that this brain region in A1$^+$ allele subjects has a significantly lower D$_2$ dopamine receptor density than in A1$^-$ allele subjects Noble et al., 1991). These observations, taken together, raise the possibility that the diminished [$^3$H]naloxone binding in the caudate nucleus of A1$^+$ allele subjects is connected with the reduced D$_2$ dopamine receptor density in the caudate nucleus.

Recent morphological studies have shown a direct dopaminergic input to the enkephalinergic neurons of the rat striatum (Kubota et al., 1986) that is mediated by D$_2$ dopamine receptors (LeMoine et al., 1990; LeMoine et al., 1991). Electron microscopy has demonstrated that many of these connections may be presynaptic in the form of dopaminergic terminals apposed to enkephalinergic axons (Pickel et al., 1992). Further, in 6-hydroxydopamine lesion and chronic D$_2$ dopamine receptor agonist studies, increased enkephalin and proenkephalin mRNA levels were found (Chritin et al., 1993; Normand et al., 1987; Soghomonian, 1993). these reports suggest that the D$_2$ dopamine receptors regulate enkephalin levels in rat striatal neurons. It is thus conceivable that the diminished inherent dopaminergic input of A1$^+$ allele subjects in the human caudate, in the form of decreased lessening of inhibitory constraints, may lead to enhanced enkephalin levels. Such an enhancement could in turn explain the reduced [$^3$H]naloxone binding in the caudate nucleus observed in this study; a phenomenon supported by the reported down-regulation of the number of δ receptors in cultured neural cells following chronic exposure to elevated levels of δ receptor agonists (Blanchard et al., 1983).

Since opiate receptor binding is differentiated in subjects with or without the DRD2 A1 allele, and because opiate receptor antagonists, such as naltrexone, have been successfully used in the treatment of a subgroup of alcoholics (O'Malley et al., 1992; Swift et al., 1994; Volpicelli et al., 1992), treatment outcome with such antagonists appears to be related to the polymorphic pattern of the DRD2 gene.

6. REFERENCES

The following literature citations as well as those cited above are incorporated in pertinent part by reference herein for the reasons cited in the above text:

Ahlenius et al., "Antagonism by Alpha Methyltryosine of the Ethanol-Induced Stimulation and Euphoria in Man," Clin. Pharmacol. Ther., 14:586–591, 1973.

Allen and Choun, "Large unilamellar liposomes with low uptake into the reticuloendothelial system," FEBS Lett., 223:42–46, 1987.

American Psychiatric Association, Committee on Nomenclature and Statistics. Diagnostic and Statistical Manual of Mental Disorders, 3rd ed., revised, American Psychiatric Association, Washington, 1987.

Amit and Brown, "Actions of Drugs of Abuse on Brain Reward Systems: A Reconsideration with Specific Attention to Alcohol," Pharmacol. Biochem. Behav., 17:233–238, 1982.

Anokhina, "Dopamine Receptor Agonists in the Treatment of Alcoholism. In: Pharmacological Treatments for Alcoholism, Edwards G, Littleton J. (eds.), New York, Mathuen, 1984.

Balazsovits et al., "Analysis of the effect of liposome encapsulation on the vesicant properties, acute and cardiac toxicities, and antitumor efficacy of doxorubicin," Cancer Chemother. Pharmacol., 23:81–86, 1989.

Balldin et al., "Neuroendocrine Evidence for Reduced Dopamine Receptor Sensitivity in Alcoholism," Alcoholism, 16:71–74, 1992.

Balldin et al., "Further Neuroendocrine Evidence for Reduced $D_2$ Dopamine Receptor Function in Alcoholism," Drug Alc. Depend., 32:159–162, 1993.

Beck, Depression Inventory, Philadelphia Center for Cognitive Therapy, Philadelphia, Penn., 1978.

Benjamin et al., "Naltrexone Reverses Ethanol-Induced Dopamine Release in the Nucleus Accumbens in Awake, Freely Moving Rats," Brain Res., 621:137–140, 1993.

Berman and Noble, "Reduced Visuospatial Performance in Children with the $D_2$ Dopamine Receptor A1 Allele," Behav. Genet., 25:45–48, 1995.

Blanchard et al. "Characterization of the association of titrated enkephalin with neuroblastoma cells under conditions for receptor down regulation," J. Biol. Chem., 258:1092–1097, 1983.

Blum et al., "Allelic Association of Human Dopamine $D_2$ Receptor Gene in Alcoholism," J. Am. Med. Assoc., 263:2055–2060, 1990.

Bohn et al., "Naltrexone and Brief Counseling to Reduce Heavy Drinking," Am. J. Addictions, 3:91–99, 1994.

Borg, "Bromocriptine in the prevention of alcohol abuse," Acta Psychiat. Scand., 68:100–111, 1983.

Borg and Weinholdt, "A Preliminary Study of Two Dopaminergic Drugs, Apomorphine and Bromocriptine (Parlodel), in the Treatment of the Alcohol-Withdrawal Syndrome," Curr. Ther. Res., 27:170–177, 1980.

Borg and Weinholdt, "Bromocriptine in the Treatment of the Alcohol-Withdrawal Syndrome," Acta Psychiat. Scand., 65:101–111, 1982.

Brodie et al., "Ethanol Increases the Firing Rate of Dopamine Neurons of the Rat," Brain Res., 508:65–69, 1990.

Brown and Amit, "The Effects of Selective Catecholamine Depletions by b 6-Hydroxydopamine on Ethanol Preference in Rats," Neurosci. Lett., 5:333–336, 1977.

Carlsson et al., "A Double-Blind Cross-Over Study: Apomorphine/Placebo in Chronic Alcoholics," Intl. J. Clin. Pharmacol. Biopharmacy, 15:211–213, 1977.

Chang and Cuatrecasas. "Multiple opiate receptors, enkephalins and morphine binding to receptors of different specificity," J. Biol. Chem., 254:2610–2618, 1979.

Chang et al. "Interactions of ligands with morphine and enkephalin receptors are differentially affected by guanine nucleotide," Mol. Pharmacol., 20:1–7, 1981.

Charness et al. "Ethanol increases the expression of functional delta-opioid receptors in neuroblastoma×glioma NG 108-15 hybrid cells," J. Biol. Chem., 261:3164–3169, 1986.

Chritin et al. "Time-course of changes in striatal levels of DA uptake sites, $D_2$ receptor and preproenkephalin mRNAs after nigrostriatial dopaminergic denervation in the rat," Mol. Brain Res., 19:319–322, 1993.

Cloninger, "Neurogenetic Adaptive Mechanisms in Alcoholism," Science, 236:410–416, 1987.

Cloninger, "$D_2$ Dopamine Receptor Gene is Associated but not Linked with Alcoholism," J. Am. Med. Assoc., 266:1833–1834, 1991.

Comings et al., "The Dopamine $D_2$ Receptor Locus as a Modifying Gene in Neuropsychiatric Disorders," J. Am. Med. Assoc., 266:1793–1800, 1991.

Comings et al., "The Dopamine $D_2$ Receptor Gene: A Genetic Risk Factor in Substance Abuse," Drug Alc. Depend., 34:175–180, 1994.

Cook and Gurling, "The $D_2$ Dopamine Receptor Gene and Alcoholism: A Genetic Effect on the Liability for Alcoholism," J. Royal Soc. Med., 87:400–402.

Corcoran et al., "Forebrain Noradrenaline and Oral Self-Administration of Ethanol by Rats," Behav. Brain Res., 8:1–21, 1983.

Coune, "Liposomes as drug delivery system in the treatment of infectious deseases: potential applications and clinical experience," Infection 16(3):141–147, 1988.

Couvreur, "Polyalkyleyanoacrylates as colloidal drug carriers," Crit. Rev. Ther. Drug Carrier Syst., 5:1–20, 1988.

Couvreur et al., "Nanocapsules, a new lysosomotropic carrier," FEBS Lett., 84:323–326, 1977.

Davis et al., "Reinforcement with Intragastric Infusions of Ethanol: Blocking Effect of FLA-57," Pharmacol. Biochem. Behav., 11:545–548, 1979.

Dongier et al., "Bromocriptine in the Treatment of Alcohol Dependence," Alcoholism, 15:970–977, 1991.

Dyr et al., "Effects of $D_1$ and $D_2$ Dopamine Receptor Agents on Ethanol Consumption in the High-Alcohol-Drinking (HAD) Lines of Rats," Alcohol, 10:207–212, 1993.

Faller and Baltimore, "Liposome encapsulation of retrovirus allows efficient super infection of resistant cell lines," J. Virol., 49(1):269–272, 1984.

Feldman, "Apomorphine in the Treatment of Alcohol Addiction: Neurophysiological and Therapeutic Aspects," Psychiat. J. Univ. Ottawa, 8:30–37, 1983.

Gabizon and Papahadjopoulos, "Liposomes formulations with prolonged circulation time in blood and enhanced uptake by tumors," Proc. Natl. Acad. Sci. USA, 85:6949–6953, 1988.

Gejman et al., "No Structural Mutation in the Dopamine $D_2$ Receptor Gene in Alcoholism or Schizophrenia," J. Am. Med. Assoc., 271:204–208, 1994.

Gelernter et al., "The A1 Allele of the D2 Dopamine Receptor Gene and Alcoholism," J. Am. Med. Assoc., 269:1673–1677, 1993.

Gessa et al., "Low Doses of Ethanol Activate Dopaminergic Neurons of the Ventral Tegmental Area," Brain Res., 248:201–203, 1985.

Gianoulakis. "Long term ethanol alters the binding of $^3$H-opiates to brain membranes," Life Sci., 33:725–733, 1983.

Gianoulakis. "The effect of ethanol on the biosynthesis and regulation of opioid peptides. Experientia 45:428–435, 1989.

Gongwer et al., "Regional Brain Contents of Serotonin, Dopamine and Their Metabolites in the Selectively Bred High- and Low-Alcohol Drinking Lines of Rats," *Alcohol*, 6:317–320, 1989.

Gordis, "Neurochemistry of Craving Provides Basis for Pharmacological Intervention," *J. Am. Med. Assoc.*, 272:1733, 1994.

Gorelick, "Medications for the Treatment of Substance Abuse," *Curr. Opin. Psychiatr.*, 5:430–435, 1992.

Gorwood et al., Are Genes Coding for Dopamine Receptors Implicated in Alcoholism?" *Europ. Psychiatry*, 9:63–69, 1994.

Heath et al., "Liposome-mediated delivery of pteridine antifolates to cells: in vitro potency of methotrexate and its alpha and gamma substituents," *Biochim. Biophys. Acta*, 862:72–80, 1986.

Heath and Martin, "The development and application of protein-liposome conjugation techniques," *Chem. Phys. Lipids* 40:347–358, 1986.

Heinz et al., "Blunted Growth Hormone Response is Associated with Early Relapse in Alcohol-Dependent Patients," *Alcoholism*, 19:62–65, 1995.

Henry-Michelland et al., "Attachment of antibiotics to nanoparticles; Preparation, drug-release and antimicrobial activity in vitro, *Int. J. Pharm*, 35:121–127, 1987.

Hietela et al., "Striatal $D_2$ Dopamine Receptor Binding Characteristics In Vivo in Patients with Alcohol Dependence," *Psychopharmacology*, 116:285–290, 1994.

Hwang et al., "Increased Number of GABAergic Terminals in the Nucleus Accumbens is Associated with Alcohol Preference in Rats," *Alcoholism*, 14:503–507, 1990.

Hynes et al. "Chronic ethanol alters the receptor binding characteristics of the delta opioid receptor ligand, D-Ala$^2$, D-Leu$^5$ enkephalin in mouse brain," *Life Sci.*, 33:2331–2337, 1983.

Imaizumi et al., "Liposome-entrapped superoxide dismutase reduces cerebral infarction in cerebral ischemia in rats," *Stroke*, 21(9):1312–1317, 1990a.

Imaizumi et al., "Liposome-entrapped superoxide dismutase ameliorates infarct volume in focal cerebral ischemia," *Acta. Neurochirurgica Suppl.*, 51:236–238, 1990b.

Imperato and Di Chiara, "Preferential Stimulation of Dopamine Release in the Nucleus Accumbens of Freely Moving Rats by Ethanol," *J. Pharmacol. Exp. Ther.*, 239:219–239, 1986.

Jellinek, *The Disease Concept of Alcoholism*, Hillhouse Press, New Haven, Conn., 1960.

Kessler et al. "Identification of extrastriatal dopamine $D_2$ receptors in post mortem human brain with [$^{125}$I] epidepride," *Brain Res.*, 609:237–243, 1993.

Koob and Bloom. "Cellular and molecular mechanisms of drug dependence," *Science* 242:715–723, 1988.

Koob, "Drugs of Abuse: Anatomy, Pharmacology and Function of Reward," *Trends Pharmacol. Sci.*, 13:177–184, 1992.

Kubota et al. "ultrastructural evidence of dopamninergic input to enkephalinergic neurons in rat neostriatum," *Brain Res.*, 367:374–378, 1986.

Kuhar et al. "Regional distribution of opiate receptor binding in monkey and human brain," *Nature* 245:447–450, 1973.

Lawford et al., "Bromocriptine in the treatment of alcoholics with the $D_2$ dopamine receptor A1 allele," *Nature Med.*, 1:337–341, 1995.

Le et al. "The effects of selective blockade of delta and mu opiate receptors on ethanol consumption by C57BL/6 mice in restricted access paradigm," *Brain Res.*, 630:330–332, 1993.

Le Moine et al. "Dopamine receptor gene expression by enkephalin neurons in rat forebrain," *Proc. Natl. Acad. Sci. USA*, 87:230–234, 1990.

Le Moine et al. "Phenotypical characterization of the rat striatal neurons expressing the $D_1$ dopamine receptor gene," *Proc. Natl. Acad. Sci. USA*, 88:4205–4209, 1991.

Levy et al., "Microinjection of Sulpiride into the Nucleus Accumbens Increases Ethanol Drinking in Alcohol Preferring (P) Rats," *Alcohol Alcohol*, Suppl 1:417–420, 1991.

Liskow and Goodwin, "Pharmacological Treatment of Alcohol Intoxication, Withdrawal and Dependence: A Critical Review," *J. Stud. Alcohol*, 48:356–370, 1987.

Litten and Allen, "Pharmacotherapies for Alcoholism: Promising Agents and Clinical Issues," *Alcoholism*, 15:620–633, 1991.

Lopez-Berestein et al., "Liposomal amphotericin B for the treatment of systemic fungal infections in patients with cancer: a preliminary study" *J. Infect. Dis.*, 2151:704, 1985a.

Lopez-Berestein et al., "Protective effect of liposomal-amphotericin B against C albicans infection in mice," *Cancer Drug Delivery*, 2:183, 1985b.

Lopez-Ibor-Alino et al., "Maintenance Treatment for Opiate Dependence at a Naltrexone Clinic," *Actas Luso Esp Neurol Psiquiatr Cienc Afines*, 18:296–305, 1990.

Lowry et al. "Protein measurement with folin phenol reagent," *J. Biol. Chem.*, 193:265–275, 1951.

Lucchi et al. "Chronic ethanol induces changes in opiate receptor function and in metenkephalin release," *Alcohol*, 2:193–195, 1985.

Mason et al., "A Double-Blind, Placebo-Controlled Pilot Study to Evaluate the Efficacy and Safety of Oral Nalinefene HCl for Alcohol Dependence," *Alcoholism*, 18:1162–1167, 1994.

McBride et al., "Densities of Dopamine $D_2$ Receptors are Reduced in CNS Regions of Alcohol-Preferring P Rats," *Alcohol*, 10:387–390, 1993.

McBride et al., "Effects of Ro-15-4513, Fluoxetine and Desipramine on the Intake of Ethanol, Water and Food by the Alcohol-Preferring (P) and Non-Preferring (NP) Lines of Rats," *Pharmacol. Biochem. Behav.*, 10:1045–1050, 1988.

McBride et al., "Serotonin, Dopamine and GABA Involvement in Alcohol Drinking of Selectively Bred Rats," *Alcohol*, 7:199–205, 1990.

Morgan et al., "Successful Use of Bromocriptine in the Treatment of Chronic Hepatic Encephalopathy," *Gastroenterology*, 78:663–670, 1980.

Morgan, "Bromocriptine in the Treatment of Chronic Encephalopathy and its Effects on the Handling of Alcohol by Control Subjects and Alcoholics," *Res. Clin. Forums*, 339:47, 1981.

Mori and Fukatsu, "Anticonvulsant effect of DN-1417 a derivative of thyrotropin-releasing hormone and liposome-entrapped DN-1417 on amygdaloid-kindled rats," *Epilepsia*, 33(6):994–1000, 1992.

Morris et al. "Dopaminergic regulation of striatal proenkephalin mRNA and prodynorphin mRNA: contrasting effects of $D_1$ and $D_2$ antagonists," *Neuroscience*, 25:525–532, 1988.

Muller et al., "Efficient transfection and expression of geterologous genes in PC12 cells," *DNA Cell Biol.*, 9(3):221–229, 1990.

Murphy et al., "Contents of Monoamines in Forebrain Regions of Alcohol-Preferring (P) and Non-Preferring (NP) Lines of Rats," *Pharmacol. Biochem. Behav.*, 26:389–392, 1987.

Murphy et al., "Effects of Fluoxetine on the Intragastric Self-Administration of Ethanol in the Alcohol Preferring P Line of Rats," *Alcohol*, 5:283–286, 1988.

Murphy et al., "Monoamine Uptake Inhibitors Attenuate Ethanol Intake in Alcohol-Preferring (P) Rats," *Alcohol*, 2:39–53, 1985.

Myers et al. "Antagonism by naltrexone of voluntary alcohol selection in the chronically drinking macaque monkey," *Alcohol*, 3:383–386, 1986.

Nicolau and Gersonde, "Incorporation of inositol hexaphosphate into intact red blood cells, I. fusion of effector-containing lipid vesicles with erythrocytes," *Naturwissenschaften* (Germany) 66(11):563–566, 1979.

Noble, "Pharmacotherapy in the Detoxification and Treatment of Alcoholism. *In: Psychiatry Update: The American Psychiatric Association Annual Review Vol. III*, Grinspoon L (ed), Washington: American Psychiatric Press, pp. 346–359, 1984.

Noble, "The $D_2$ Dopamine Receptor Gene: A Review of Association Studies in Alcoholism," *Behav. Genet.*, 23:119–129, 1993.

Noble and Blum, "Alcoholism and the $D_2$ Receptor Gene (Letter)," *J. Am. Med. Assoc.*, 270;1547, 1993.

Noble et al., "Allelic Association of the $D_2$ Dopamine Receptor Gene with Receptor-Binding Characteristics in Alcoholism," *Arch. Gen. Psychiatr.*, 48:648–654, 1991.

Noble et al., "Allelic Association of the $D_2$ Dopamine Receptor Gene with cocaine Dependence," *Drug Alc. Depend.*, 33:271–285, 1993.

Noble et al. "Prolonged P300 latency in children with the $D_2$ dopamine receptor A1 allele," *Am. J. Hum. Genet.*, 54:658–668, 1994a.

Noble et al. "$D_2$ dopamine receptor gene and obesity," *Int. Eating Disord.*, 15:205–217, 1994b.

Noble et al., "Allelic Association of the Human D2 Dopamine Receptor Gene with Obesity," *Int. J. Eating Disorders*, 15:205–217, 1994c.

Noble et al., "$D_2$ Dopamine Receptor Gene and Cigarette Smoking: A Reward Gene?" *Med. Hypotheses*, 42:257–260, 1994d.

Noble et al., "Prolonged P300 Latency in Children with the $D_2$ Dopamine Receptor A1 Allele," *Am. J. Hum. Genet.*, 54:658–668, 1994e.

Normand et al. "Anatomical study of enkephalin gene expression in the rat forebrain following haloperidol treatment," *Neurosci. Lett.*, 83:232–236, 1987.

Normand et al. "Dopamine neurons in the substantia nigra modulate proenkephalin A gene expression in rat striatal neurons," *Brain Res.*, 439:39–40, 1988.

O'Malley et al., "Naltrexone and Coping Skills Therapy for Alcohol Dependence," *Arch. Gen. Psychiatry*, 49:881–887, 1992.

Pfeiffer et al. "Opiate receptor binding sites in human brain," *Brain Res.*, 248:87–96, 1982.

Pickel et al. "Cellular basis for interactions between catecholaminergic afferents and neurons containing Leu-enkephalin-like immunoreactivity in rat caudate-putamen nuclei," *J. Neurosci. Res.*, 31:212–230, 1992.

Pikul et al., "In vitro killing of melanoma by liposome-delivered intracellular irradiation, *Arch. Surg.* 122(12):1417–1420, 1987.

Powell et al., "A Double-Blind, Placebo-Controlled Study of Nortriptyline and Bromocriptine in Male Alcoholic Subtyped by Comorbid Psychiatric Disorders," *Alcoholism*, 19:463–468, 1995.

Prato et al., "Review of the Putative Association of DRD2 and Alcoholism. A Meta-Analysis," *Am. J. Hum. Genet.*, 48:78–82, 1993.

Quarfordt et al., "Ethanol Drinking Following 6-OHDA Lesions of Nucleus Accumbens and Tuberculum Olfactorium of the Rat," *Alcohol*, 8:211–217, 1991.

Rassnick et al., "SDZ-205,152, a Novel Dopamine Receptor Agonist, Reduces Oral Ethanol Self-Administration in Rats," *Alcohol*, 10:127–132, 1993.

Reese, "Changing Patients' Health Beliefs to Improve Compliance with Alcoholism Treatment: A Controlled Trial," *J. Stud. Alcohol*, 47:436–439, 1986.

Ritchie and Noble. "[$^3$H]Naloxone binding in the human brain: alcoholism and the TaqI A $D_2$ dopamine receptor polymorphism," *Brain Res.*, 718:193–197, 1996.

Saiki et al. "Primer-directed enzymatic amplification of DNA with thermostable DNA polymerase," *Science*, 239:487491, 1988.

Sculier et al., "Pilot study of amphotericin B entrapped in sonicated liposomes in cancer patients with fungal infections," *J. Cancer Clin. Oncol.*, 24(3):527–538, 1988.

Seizinger et al. "Differential effects of acute and chronic ethanol treatment on particular opioid peptide systems in discrete regions of rate brain and pituitary," *Pharmacol. Biochem. Behav.*, 18:361–369, 1983.

Simantov et al. "The opiate receptor binding interactions of $^3$H-methionine enkephalin, an opioid peptide," *Eur. J. Pharmacol.*, 47:319–331, 1978.

Smith et al., "Genetic Vulnerability to Drug Abuse: The Dopamine $D_2$ Receptor TaqI B1 Restriction Fragment Length Polymorphism Appears More Frequently in Polysubstance Abusers," *Arch. Gen. Psychiatry*, 49:723–727, 1992.

Soghomoniam. "Effects of neonatal 6-hydroxydopamine injections on glutamate decarboxylase, preproenkephalin and dopamine $D_2$ receptor mRNA in the adult rat striatum," *Brain Res.*, 621:249–259, 1993.

Spielberger, *Manual for the State-Trait-Anxiety Inventory (Form Y)*. Consulting Psychologist Press, Palo Alto, Calif., 1983.

Stefanini et al., "Alcohol-Preferring Rats Have Fewer Dopamine $D_2$ Receptors in the Limbic Area," *Alcohol Alcohol.*, 27:127–130, 1992.

Swift et al., "Naltrexone-Induced Alterations in Human Ethanol Intoxication,"*Am. J. Psychiatry*, 151:1463–1467, 1994.

Tempel et al. "Neurochemical and functional correlates of naltrexone-induced opiate receptor upregulation," *J. Pharmacol. Exp. Ther.*, 232:439–444, 1985.

Tiihonen et al., "Altered Striatal Dopamine Re-Uptake Site Densities in Habitually Violent and Non-Violent Alcoholics," *Nature Med.*, 1:654–657, 1995.

Uhl et al., "Substance Abuse Vulnerability and $D_2$ Receptor Gene," *Trends Neurosci.*, 16:83–88, 1993.

Volpicelli et al. "Alcohol drinking in rats during and following morphine injections," *Alcohol*, 8:289–292, 1991.

Volpicelli et al., "Naltrexone in the Treatment of Alcohol Dependence," *Arch. Gen. Psychiatry*, 49:876–880, 1992.

Volpicelli et al., "Effects of Naltrexone on Alcohol "High" in Alcoholics," *Am. J. Psychiatry*, 152:613–615, 1995.

Weiss et al., "Free-Choice Responding for Ethanol Versus Water in Alcohol Preferring (P) and Unselected Wistar Rats is Differentially Modified by Naloxone, Bromocriptine and Methysergide," *Psychopharmacology*, 101:178–186, 1990.

Weiss et al., "Oral Alcohol Self-Administration Stimulates Dopamine Release in the Rat Nucleus Accumbens: Genetics and Motivational Determinants," *J. Pharmacol. Exp. Ther.*, 267:250–258, 1993.

Widdowson and Holman. "Ethanol-induced increase on endogenous dopamine release may involve endogenous opiates," *J. Neurochem.*, 59:157–163, 1992.

Wiesbeck et al., "Alcohol dependence, family history, and D2 dopamine receptor functions as neuroendocrinologically assessed with apomorphine," *Drug Alcohol Depend.*, 40:49–53, 1995.

Wild and Reid. "Modulation of ethanol-intake by morphine: evidence for a central site of action," *Life Sci.*, 47:PL49–54, 1990.

Wise and Rompre, "Brain Dopamine and Reward," *Ann. Rev. Psychol.*, 40;191–225, 1989.

Wozniak et al., "Focal Application of Alcohol Elevates Extracellular Dopamine in Rat Brain: A Microdialysis Study," *Brain Res.*, 540:31–40, 1991.

Yoshimoto et al., "Alcohol Stimulates the Release of Dopamine and Serotonin in the Nucleus Accumbens," *Alcohol*, 9:17–22, 1991.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims. Accordingly, the exclusive rights sought to be patented are as described in the claims below.

What is claimed is:

1. A method of alleviatig alcohol addiction in a human having a $D_2$ dopamine receptor A1 allele, the method comprising the steps of:

(a) obtainig nucleic acids from a blood sample of said human (b) identifying in said nucleic acids a $D_2$ dopamine receptor A1 allele; and (c) administering to said human an amount of DRD2-specific dopamine agonist sufficient to alleviate said alcohol addiction, wherein said dopamine agonist is bromocriptine.

2. The method of claim 1, wherein said A1 allele is present in an A1/A1 genotype.

3. The method of claim 1, wherein said A1 allele is present in an A1/A2 genotype.

4. The method of claim 1, further comprising administering to said human a serotonin reuptake inhibitor selected from the group consisting of fluoxetine, sertraline, paroxetine, fluvoxamine, venlafaxine, and nefazodone.

* * * * *

UNITED STATES PATENT AND TRADEMARK OFFICE
CERTIFICATE OF CORRECTION

PATENT NO.    :    6,001,848
DATED         :    December 14, 1999
INVENTOR(S)   :    Ernest P. Noble It is certified that error appears in the above-identified patent and that said Letters Patent is hereby corrected as shown below:

Claim 1, column 36, line 7, delete "alleviatig" and replace with --alleviating--.

Claim 1, column 36, line 11, delete "obtainig" and replace with --obtaining--.

Signed and Sealed this

Twentieth Day of June, 2000

*Attest:*

Q. TODD DICKINSON

*Attesting Officer*        *Director of Patents and Trademarks*